(12) United States Patent
Bayley et al.

(10) Patent No.: US 6,824,659 B2
(45) Date of Patent: Nov. 30, 2004

(54) DESIGNED PROTEIN PORES AS COMPONENTS FOR BIOSENSORS

(75) Inventors: Hagan Bayley, College Station, TX (US); Orit Braha, College Station, TX (US); John Kasianowicz, Darnestown, MD (US); Eric Gouaux, New York, NY (US)

(73) Assignee: University of Massachusetts, Boston, MA (US)

( * ) Notice: Subject to any disclaimer, the term of this patent is extended or adjusted under 35 U.S.C. 154(b) by 187 days.

(21) Appl. No.: 09/784,985

(22) Filed: Feb. 15, 2001

(65) Prior Publication Data

US 2004/0191845 A1 Sep. 30, 2004

Related U.S. Application Data

(63) Continuation of application No. 09/122,583, filed on Jul. 24, 1998, now abandoned.
(60) Provisional application No. 60/053,737, filed on Jul. 25, 1997.

(51) Int. Cl.[7] ............................................. G01N 27/327
(52) U.S. Cl. ............................ 204/403.01; 204/403.08; 930/10
(58) Field of Search ............................. 205/777.5, 778; 204/403.01, 403.08; 422/68.1, 82.01, 82.05, 82.03

(56) References Cited

U.S. PATENT DOCUMENTS

| | | | |
|---|---|---|---|
| H201 H | 1/1987 | Yager | 436/151 |
| 4,867,973 A | 9/1989 | Goers et al. | 424/181.1 |
| 4,975,278 A | 12/1990 | Senter et al. | 424/178.1 |
| 5,368,712 A | * 11/1994 | Tomich et al. | 204/403.06 |
| 5,777,078 A | 7/1998 | Bayley et al. | 530/350 |

FOREIGN PATENT DOCUMENTS

| | | |
|---|---|---|
| EP | 0 185 076 B1 | 8/1992 |
| WO | WO 94/25616 | 11/1994 |

OTHER PUBLICATIONS

Kasianowicz, "Detecting and characterizing analytes with an ion channel," Book of Abstracts, 213th ACS National Meeting, San Francisco, Apr. 13–17 (1997).*
Adams et al., "Controlling Cell Chemistry with Caged Compounds," 1993, Annu. Rev. Physiol., 55:755–84.
Amato, "Molecular Design Gets Into a Hole," 1992, Science, 255:684.
Avila et al., "A New Immunotoxin Built by Linking a Hemolytic Toxin to a Monoclonal Antibody Specific for Immature T Lymphocytes," 1988, Int. J. Cancer, 42:568–71.
Avila et al., "A Carcinoembryonic Antigen–Directed Immunotoxin Built by Linking a Monoclonal Antibody to a Hemolytic Toxin," 1989, Int. J. Cancer, 43:926–29.
Bayley, "Self–Assembling Biomolecular Materials in Medicine," 1994, J. Cell. Biochem., 56:168–70.
Bayley, "Channels With Single Transmembrane Segments," 1994, News in Physiological Sciences, 9:45–46.
Bayley, "Photoactivatable Drugs," 1987, Trends in Pharmacol. Sciences, 8:138–43.
Bayley, "Triggers and Switches in a Self–Assembling Pore–Forming Protein," 1994, J. Cell. Biochem., 56:177–82.

(List continued on next page.)

*Primary Examiner*—Alex Noguerola
(74) *Attorney, Agent, or Firm*—Fish & Richardson P.C.

(57) ABSTRACT

A mutant staphylococcal alpha hemolysin polypeptide containing a heterologous analyte-binding amino acid which assembles into an analyte-responsive heptameric pore assembly in the presence of a wild type staphylococcal alpha hemolysin polypeptide, digital biosensors, and methods of detecting, identifying, and quantifying analytes are described.

25 Claims, 14 Drawing Sheets

OTHER PUBLICATIONS

Bayley, "Novel Biomaterials: Genetically Engineered Pores," 1990, Dept. of Energy Grant No. DE–FG02–9OR20018, Worcester Found, for Exptl. Biol.

Boman, "Antibacterial Peptides; Key Components Needed in Immunity," 1991, Cell, 65:205–207.

Bowie et al., "Deciphering the Message in Protein . . . ," Science, 247:1306–1310, 1990.

Braha et al., "Designed Protein Pores as Components for biosensors," 1997, Chemistry & Biology, 497–505, vol. 4, No. 7.

Brennan et al., "A Molecular Sensor System Based on Genetically Engineered Alkaline Phosphatase," 1995, Proc. Natl. Acad. Sci. 92:5783–5787.

Chang et al., "A Photogenerated Pore–Forming Protein," 1994, Chem & Biol., 2(6):391–400.

Cheley et al., "Type II Regulatory Subunits of cAMP–dependent Protein Kinase and Their Binding Proteins in the Nervous System of Aplysia californica," 1994, J. Biol. Chem., 269L:2911–20.

Chovnick et al., "A Recombinant Membrane–Acting Immunotoxin," 1991, Cancer Res., 51:465–467.

Cornell et al., "A Biosensor That Uses Ion–Channel Switches," 1997, Nature, 387:580–583, Jun. 5, 1997.

Dawson et al., "Synthesis of Proteins by native Chemical Ligation," Nov. 4, 1994, Science, 776–79, vol. 266.

Durell et al., "Theoretical Models of the Ion Channel Structure of Amyloid β–Protein," 1994, Biophys. J., 67:2137–45.

Egholm et al., "PNA hybridizes to Complementary Oligonucleotides Boeying the Watson–Crick Hydrogen–bonding Rules," 1993, Nature, 365:566–68.

Ellman et al., "Site–Specific Incorporation of Novel Backbone Structures into Protein," 1992, Science, 255:197–200.

Ericksson et al., Crystallographic Studies of Inhibitor Binding Sites in Human Carbonic Anhydrase II: A Pentacoordinated Binding of the SCN Ion to the Zinc at High pH, 1988, Proteins: Structure, Function, and Genetics, 4:283–293.

Goldmacher et al., "Photoactivation of Toxin Conjugates," 1992, Bioconjugate Chem., 3:104–107.

Gouaux et al., "Subunit Stoichiometry of Staphylococcal α–hemolysin in Crystals and on Membranes; A Heptameric Transmembrane Pore," 1994, Proc. Natl. Acad. Sci. USA, 91:1282:31.

Gray et al., "Primary Sequence of the Alpha ToxinGene from Staphylococcus Aurehs Wood 46, " 1984, Infect. Immun., 46:615–618.

Hanke et al., "Planar Lipid Bilayers" 1993, Academic Press., Table of Contents.

Harris et al., "Therapeutic Antibodies–the Coming of Age," 1993, TIBTECH, 11:42–44.

Hazum et al., "A Photocleavable Protecting Group for the Thiol Function of Cysteme," 1980, Peptides 1980: Proceedings of Sixteenth European Peptide Symposium, pp. 105–10.

Hilvert, "Extending the Chemistry of Enzymes and Abzyes," 1991, Trends Biotechnol., 9:11–17.

Hird et al., "Immunotherapy with Monoclonal Antibodies," 1990, Genes and Cancer, 17:184–189.

Huennekens, "Tumor targeting: activation of prodrugs by enzyme–monoclonal antibody conjugates," 1994, TICTECH., vol. 12.

Huston et al., "Protein Engineering of Single–Chain Fv Analogs and Fusion Proteins" 1991, Methods in Enzymology., 203:46–89.

Ippolito et al., "Structure–assisted Redesign of a Protein–Zinc–Binding Site with Femtomolar Affinity," 1995 Proc. Natl. Acad. Sci., 92:5017–5021.

Kasianowicz et al., "Genetically Engineered Pores as Metal Ion Biosensors," 1994, Mat. Res. Soc. Symp. Proc. 330:217–23.

Koltchine et al., "Homomeric Assemblies of NMDAR1 Splice Variants are Sensitive to Ethanol," 1993, Neuroscience Letters, 152:13–16.

Kraules, P.J., "MOLSCRIPT" A Program To Product Both Detailed and Schematic Plots of Protein Structures. 1991, J. Appl. Cryst., 24:946–950.

Krishnasastry et al., "Surface Labeling of Key Residues During Assembly of theStaphylococcal α–Hemolysin," 1994, FEBS Letters, 356:66–71.

Liotta et al., "Cancer Metastasis and Angiogenesis: An Imbalance of Positive and Negative Regulation," 1991, Cell, 64:327–36.

Lipkin, "Controlling Life's Gateway Opening and Closing Cell Membranes on Demand," 1994, Science News, 146:204–205.

Maiti et al., "Tolerogenic Conjugates of Xenogeneic Monoclonal Antibodies with Monomethoxypolyethylene Glycol. I. Induction. Xenogeneic Monoclonal Antibodies," 1988, Int. J. Cancer, 3:17–22.

Marriott et al., "Photomodulcation of the Nucleating Activity of a Photocleavable Crosslinked Actin Dimer," 1992, Biochemistry International, 26:943–951.

Merritt et al., "Raster3D Version 2.0 A Program for Photorealistic Molecular Graphics:," 1994, Biological Crystallography, D50:869–873.

Montal et al., "Formation of Bimolecular Membranes from Lipid Monolayers and a Study of Their Electrical Properties," Proc. Nat. Avad. Sci. USA, 69:3561–3566.

Murray, "Cyclin–dependent kinases: regulators of the cell cycle and more," 1994, Chemistry & Biology, 1:191–195.

Nielsen et al., "Sequence–Selective Recognition of DNA by Strand Displacement with a Thymine–Polyamide," 1991, Science, 254:1497–1500.

Ngo et al., "The Protein Folding Problem and Tertiary . . . ," pp. 491–495, Eds.: Mertz and Le Grand; Birkhauser, Boston, 1994.

Noren et al., A General Method for Site–Specific Incorporation of Unnatural Amino Acids into Proteins 1989, Science, 244:182–188.

Olejnik et al., "Photocleavable biotin derivatives: A Versatile Approach For the Isolation of Biomolecules," 1995, Proc. Natl. Acad. Sci. USA, 92:7590–7594.

O'Reilly et al., "Angiostatin: A Novel Angiogenesis Inhibitor That Mediates the Suppression of Metastases by a Lewis Lung Carcinoma," 1994, Cell, 79:315–328.

Osband et al. "Problems in the Investigational Study and Clinical Use of Cancer Immunotherapy," 1990 Immunology Today, 11:193–95.

Panchal et al., "Differential Phosphorylation of of Neuronal Substrates by Catalytic Subunits of cAMP–dependent Protein Kinase with Alternative N Termini," 1993, J. Biol. Chem., 269:23722–23730.

Pastan et al., "Immunotoxins," 1986, Cell 47:641–648.

Pederzolli et al., "Biochemical and Cytotoxic Properties of Conjugates of Transferrin with Equinatoxin II, a Cytolysin from a Sea Anemone," 1994, Bioconjugate Chem., 6:166:173.

Regen et al., "Supramolecular Surfactants: Amphiphillic Polymers Designed to Disrupt Lipid Membranes," 1989 Biochem. and Biophys. Res. Comm., 159:566–571.

Senter et al., "Novel Photocleavable Protein Crosslinking Reagents and Their Use in the Preparation of Anti–body–Toxin Conjugates," 1985, Photochemistry and Photobiology, 42:231–237.

Song et al., Structure of Staphlococcal α Alpha Toxin–Recent Adavnces, 1988, Toxicon, 26:51–56, Dec. 13.

Stetler et al., "The Activation of Human Type IV Collagenase Proenzyme" 1989, The Activation of Human IV Collagenase Proenzyme, 264:1353–1356.

Thelestam et al., "Staphylococcal Alpha Toxin—Recent Advances," 1988, TOXICON, 26:51–65.

Thiele and Fahrenholz, "Photocleavable Biotinylated Ligands for Affinity Chromatography:," 1994, Analytical Biochemistry, 218:330–337.

Thompson et al., "Photocleavable Nitrobenzyl–Protein Conjugates," 1993, Biochem. and Biophys. Res. Comm., 201:1213–1219.

Thompson et al., "Enzyme–Based Fiber Optic Zinc Biosensor," 1993, American Chemical Society., 65:730–734.

Tobkes et al., "Secondary Structure and Assembly Mechanism of an Oligomeric Channel Protein," 1985, Biochemistry, 24:1915–1919.

Vivaudou et al., "Skeletal Muscle ATP–Sensitive K+ Channels Recorded from Sarcolemmal Blebs of Split Fibers: ATP Inhibition is Reduced by Magnesium and ADP," 1991, J. Membrane Biol., 122:165–175.

Walker et al., "Restoration of pore–forming activity in staphylococcal α–hemolysin by targeted covalent modification," 1995, Protein Engineering, 8:491–495.

Walker et al., "Genetically–Engineered Protease–Activated Triggers in a Pore–Forming Protein," 1994 Mat. Res. Soc. Symp. Proc., 330:209–215.

Walker et al., "An intermediate in the Assembly of a Pore–Forming Protein Trapped with a Genetically–Engineered Switch," 1995, Chemistry & Biology, 2:99–105.

Walker et al., "A pore–forming Protein with a Metal–Actuated Switch," 1994, Protein Engineering, 7:655–662.

Walker et al., "A pore–forming protein with a protease–activated trigger," 1994, Protein Engineering, 7:91–97.

Walker et al., "Assembly of the Oligomeric Membrane Pore Formed by Staphylococcal α–Hemolysin Examined by Truncation Mutagenesis," 1992, J. Biol. Chem., 267:21782–21786.

Walker et al., "Functional Expression of the α–Hemolysin of Staphylococcus Aureus in Intact Echerichia Coli and in Cell Lysates," 1992, J. Biol. Chem., 267:10902–10909.

Walker et al., "Functional Complementation of Staphylococcal α–Hemolysin Fragments," 1993, J. Biol. Chem., 268:5285–5292.

Walker et al., "Key residues for membrane binding, oligomerization . . . ," J. Biol. Chem., 270:23065–23071.

Wells, "Additivity of Mutational Effects in Proteins," Biochemistry, 29:8509–8517–1990.

Wittung et al., "DNA–like double helix formed by peptide nucleic acid," 1994, Nature, 368:561–563 Apr. 7, 1999.

Zorn et al., "Halothane Acts on Many Potassium Channels, Including a Minimal Potassium Channel," 1993, Neuroscience Letters, 161:81–84.

* cited by examiner

|  | 5:1 | 1:1 | 1:5 |
|---|---|---|---|
| WT$_7$ | 27.9 | 0.78 | 0.0003 |
| WT$_6$MUT$_1$ | 39.1 | 5.47 | 0.013 |
| WT$_5$MUT$_2$ | 23.4 | 16.4 | 0.19 |
| WT$_4$MUT$_3$ | 7.81 | 27.3 | 1.56 |
| WT$_3$MUT$_4$ | 1.56 | 27.3 | 7.81 |
| WT$_2$MUT$_5$ | 0.19 | 16.4 | 23.4 |
| WT$_1$MUT$_6$ | 0.013 | 5.47 | 39.1 |
| MUT$_7$ | 0.0003 | 0.78 | 27.9 |

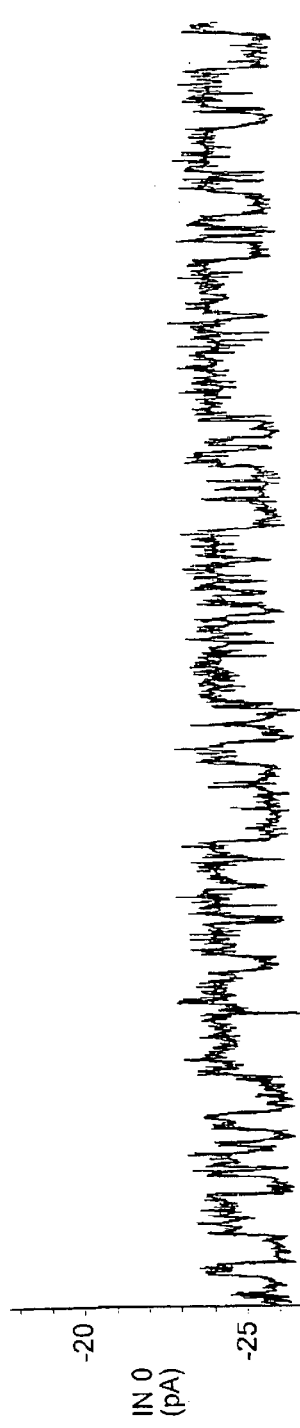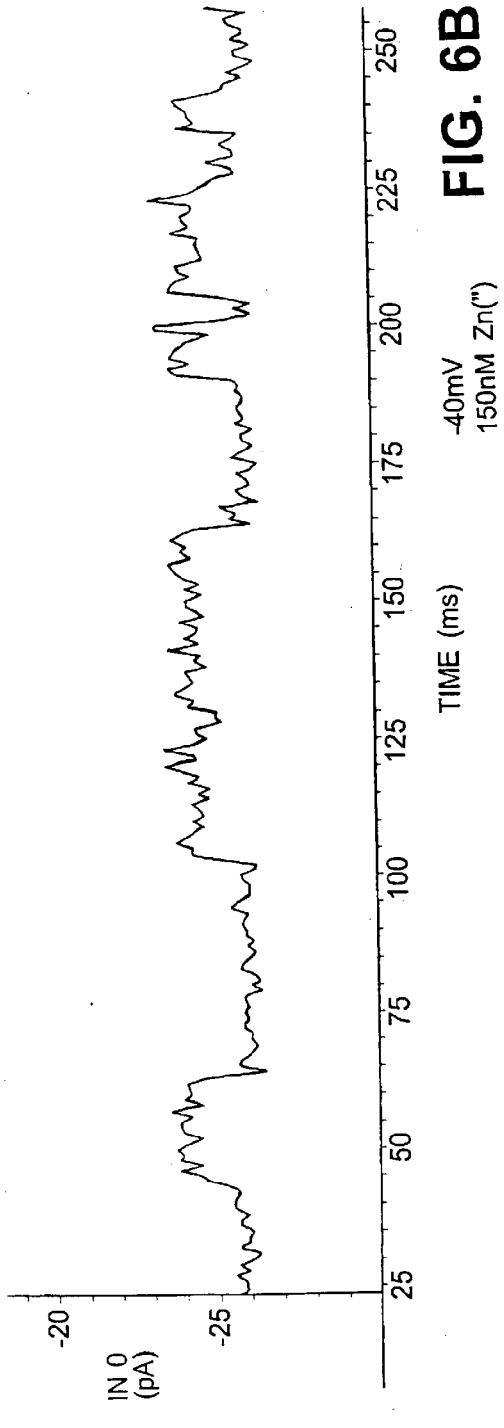
FIG. 6A
FIG. 6B

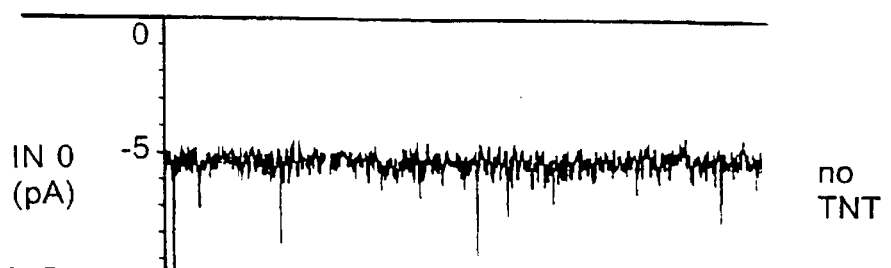
FIG. 8A
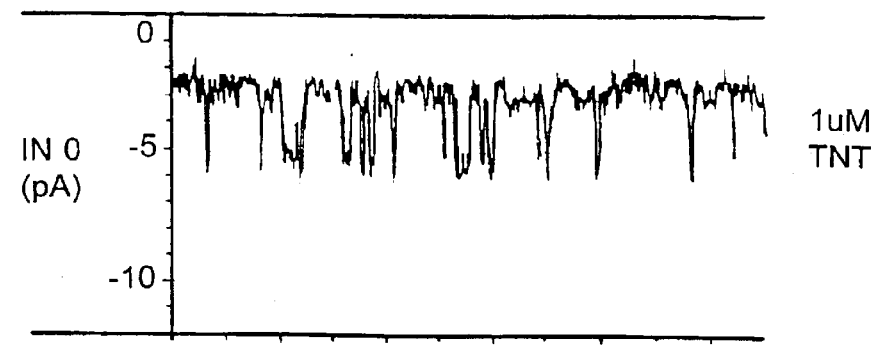
FIG. 8B  ~ 0.25ppm

DESIGNED PROTEIN PORES AS COMPONENTS FOR BIOSENSORS

CROSS-REFERENCE TO RELATED APPLICATIONS

This application is a continuation of U.S. application Ser. No. 09/122,583, filed on Jul. 24, 1998, now abandoned, which claims priority from U.S. provisional application Ser. No. 60/053,737, filed on Jul. 25, 1997, both of which are incorporated herein by reference in their entirety.

This invention was made with U.S. Government support under the Office of Naval Research grant No. N10014-93-1-0962. The government has certain rights in this invention.

BACKGROUND OF THE INVENTION

The field of the invention is metal detection.

Biosensors are analytical devices that convert the concentration of an analyte into a detectable signal by means of a biologically-derived sensing element. Well-known biosensors include commercial devices for sensing glucose. In addition, true biosensors, biomimetric devices, and devices that use living cells have recently been developed. For example, to detect divalent metal cations, true biosensors have been made using the enzyme carsonic anhydrase (Thompson et al., 1993, Anal. Chem. 65: 730–734), the metal binding site of which has been altered (Ippolito et al., 1995, Proc. Natl. Acad. Sci. USA. 92:5017–5020). To monitor HIV antibody levels, the enzyme alkaline phosphatase into which an HIV epitope has been inserted has been utilized (Brennan et al., 1995, Proc. Natl. Acad. Sci. USA 92:5783–5787).

SUMMARY OF THE INVENTION

The invention features a mutant staphylcoccal alpha hemolysin (αHL) polypeptide containing heterologous metal-binding amino acid. The polypeptide assembles into a heteroheptameric pore assembly in the presence of a wild type (WT) αHL polypeptide. Preferably, the metal-binding amino acid occupies a position in a transmembrane channel of the heteroheptameric pore assembly, e.g., an amino acid in the stem domain of WT αHL is substituted with a heterologous metal-binding amino acid. More preferably, metal-binding amino acid projects into the lumen of the transmembrane channel.

By the term "heterologous amino acid" is meant an amino that differs from the amino acid at the corresponding site in the amino acid sequence of WT αHL. By "analyte-binding amino acid" is meant any amino acid having a functional group which covalently or non-covalently binds to an analyte. By "transmembrane channel" is meant the portion or an αHL polypeptide that creates a lumen through a lipid bilayer. The transmembrane channel of an αHL pore assembly is composed of 14 anti-parallel β strands (the "β barrel"), two of which are contributed by the stem domain of each αHL polypeptide of the pore. By "stem domain" is meant the portion of an αHL polypeptide which scans approximately amino acids 110 to 150 of SEQ ID NO:1 (see, e.g., FIG. 1F)

An αHL polypeptide containing at least two non-consecutive heterologous metal-binding amino acids in a stem domain of αHL is also within the invention. By "metal-binding amino acid" is meant any amino acid which covalently or noncovalently binds to a metal ion, e.g., Ser, Thr, Met, Tyr, Glu, Asp, Cys, or His. Unnatural amino acids, such as 1,2,3 triazole-3-alanine and 2-methyl histidine, which have altered $pK_a$ values, sceric properties, and arrangement of N atoms resulting in different abilities to bind metal ions, can also be introduced to confer metal-responsiveness. Preferably, the heterologous amino acids project into the lumen of the transmembrane channel, i.e., the amino acids occupy two or more of the following positions of SEQ ID NO:1: 11, 113, 115, 117, 119, 121, 123, 125, 127, 129, 131, 133, 135, 137, 139, 141, 143, 145, 147 or 149. Alternatively, the heterologous amino acids are located on the outside of the transmembrane channel, i.e., the amino acids occupy two or more of the following positions of SEQ ID NO:1: 110, 112, 114, 116, 118, 120, 122, 124, 126, 128, 130, 132, 134, 136, 138, 140, 142, 144, 146, 148. The polypeptide may contain at least three non-consecutive heterologous metal-binding amino acids in the stem domain. Preferably, the polypeptide contains at least 4 non-consecutive heterologous metal-binding amino acids in the stem domain; more preferably, the amino acids occupy positions 123, 125, 133, and 135 of SEQ ID NO:1; more preferably, each these positions are occupied by the heterologous metal-binding amino acid His; and most preferably, the polypeptide is the αHL mutant 4H, as described below.

To facilitate separation and purification of mutant analyte-responsive αHL polypeptides, the polypeptide may also contain a heterologous amino acid, e.g., a Cys residue, at a site distant from the stem domain, e.g., at position 292 of SEQ ID NO:1.

The invention also features a heteromeric pore assembly containing a metal-responsive (M) αHL polypeptide, e.g., a pore assembly which contains a wild type (WT) staphylococcal αHL polypeptide and a metal-responsive αHL polypeptide in which a heterologous metal-binding amino acid of the metal-responsive αHL polypeptide occupies a position in a transmembrane channel of the pore structure. For example, the ratio of WT and M αHL polypeptides is expressed by the formula $WT_{7-n}M_n$, where n is 1, 2, 3, 4, 5, 6, or 7; preferably the ratio of αHL polypeptides in the heteroheptamer is $WT_{7-n}4H_n$; most preferably, the ratio is $WT_6 4H_1$. Homomeric pores in which each subunit of the heptomer is a mutated αHL polypeptide (i.e., where n=7) are also encompassed by the invention.

Also within the invention is a digital biosensor device comprising a heteromeric αHL pore assembly. The device detects binding of a metal ion to a heterologous amino acid through a single channel (single current) or through two or more channels (macroscopic current). Rather than containing a heterologous amino acid substitution, the metal-responsive αHL polypeptide in the device may contain a chelating molecule associated with an amino acid in the stem domain.

The analyte-responsive αHL polypeptides (and pore assemblies containing such polypeptides) can be used in a method of detecting the presence of an analyte, e.g., a metal such as a divalent Group IIB and transition metal. Zn(II), Co(II), Cu(II), Ni(II), or Cd(II) can be detected using the methods described herein. For example, a detection method may include the steps of (a) contacting the sample to be analyzed with an analyte-responsive αHL pore assembly, and (b) detecting an electrical current in a digital mode through a single channel (single current) or two or more channels (macroscopic current). A modulation or perturbation in the current detected compared to a control current measurement, i.e., a current detected in the absence of the analyte indicates the presence (and concentration) of the analyte.

The invention also includes a method of identifying an unknown analyte in a mixture of analytes which includes the following steps: (a) contacting the mixture with an analyte-responsive αHL pore assembly; (b) detecting an electrical current in a digital mode through a single channel (or through two or more channels) to determine a mixture current signature; and (c) comparing the mixture current signature to a standard current signature of a known analyte. A concurrence of the mixture current signature with the standard current signature indicates the identity of the unknown analyte in the mixture.

Other features and advantages of the invention will be apparent from the following description of the preferred embodiments thereof, and from the claims. All references cited herein are incorporated by reference in their entirety.

BRIEF DESCRIPTION OF THE DRAWINGS

FIG. 4B is a series of graphs showing digital single channel recordings using a $WT_7$ pore assembly (band 1 in FIG. 4A) The channel is open with an amplitude of −26.7 pA (mean=27.0±2.5 pA, n=B). Zn(II) had no effect on the current, even when increased to 500 µM.

FIG. 4C is a series of graphs showing digital single channel recordings using a $WT_6 4H_1$, pore assembly (band 2 in FIG. 4A). In the presence of 100 µM EDTA the channel is open with an amplitude of −28.4 pA at −40 mV (mean= 26.3±1.6 pA, n=7). The addition of 150 µM Zn(II) to the trans chamber results in discrete fluctuations between two open states, the original state (−28.4 pA) and another of −25.7 pA (mean=−24.4±1.8 pA, n=7). The ratio of the conductance of the new state to the conductance of the original state ($g/g_o$) was 0.93±0.01 (n=7).

FIG. 4D is a series of graphs of digital single channel recordings showing the dependence of the partial channel block of the heteromeric pore $WT_6 4H_1$ on Zn(II) concentration. Single-channel current recordings were made at various trans free Zn(II) concentrations. A solution containing 1 M NaCl, 50 mM MOPS, pH 7.5, Zn(II) was buffered with 100 µM pyridine-2,6-dicarboxylic acid and 10 µM EDTA. All points amplitude histograms are shown below each graph. The histograms can be fitted to the sum of two Gaussian functions, suggesting two distinct states: (i) the fully open channel as seen in the absence of Zn(II), (ii) the partly closed, $g/g_o$=0.93, Zn(II) dependent substrate. The normalized areas of the Gaussian functions represent the occupancy of each state at the displayed Zn(II) concentration. When the openings or closing are short, the amplitudes of the transitions are underestimated, resulting in shifts of the peaks to lower values, for example, for 190 nM Zn(II).

FIG. 6A is a graph of a digital single channel recording from $WT_6 4H_1$ in the presence of 150 nM Zn(II).

FIG. 6B is a graph showing an expanded view of a portion of the graph in FIG. 6A.

FIGS. 8A and 8B are graphs of digital single channel recordings using a pore assembly containing a 123W/135W subunit in the presence and absence of a solution containing the explosive trinitrotoluene (TNT). FIG. 8A is a recording from pores in the absence of TNT, and FIG. 8B is a recording from pores in the presence of 1 µM TNT.

DESCRIPTION OF THE PREFERRED EMBODIMENTS

Figure 1A:
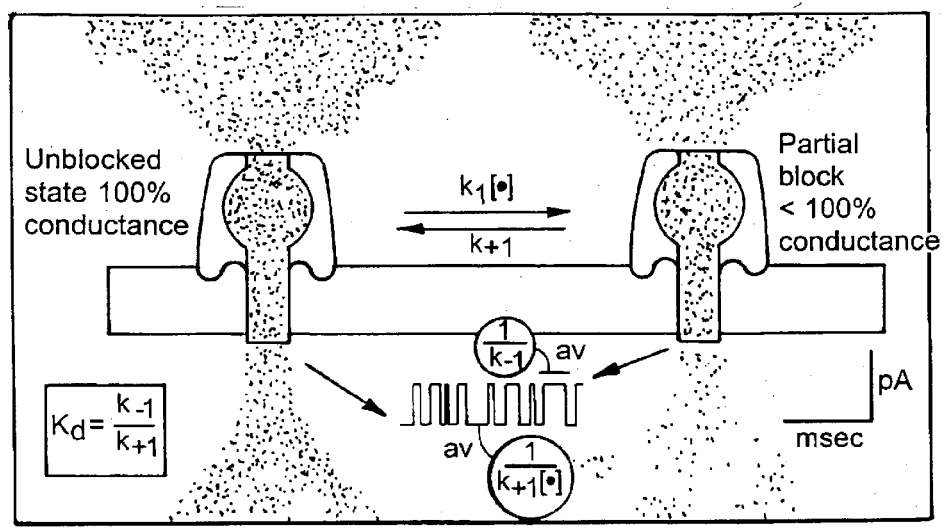
FIG. 1A is a diagram showing the interpretation of a digital/stochastic response of a single channel (patch clamp) recording using an analyte-responsive αHL pore assembly (the average upspike time durations →$K_1$, the analyte identity; the average downspike durations →[●], the analyte concentration).
Figure 1B:
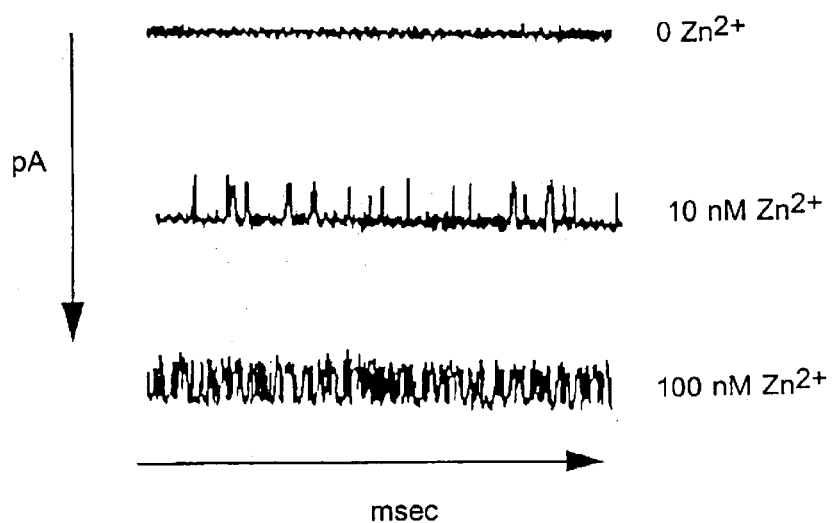
FIG. 1B is a series of graphs of digital single channel recordings showing metal-responsiveness of an αHL pore assembly at various concentrations of Zn(II).
Figure 1C:
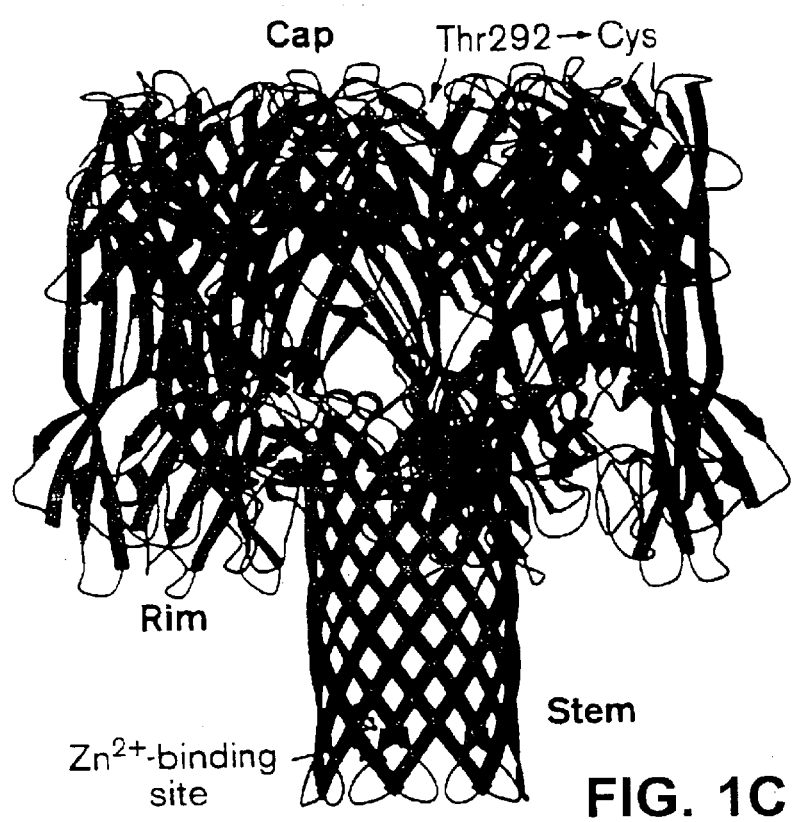
FIG. 1C is a diagram of the structure of a heteromeric αHL pore (WT$_4$4H$_1$ assembly showing a Zn(II) binding sit with a view of the heptamer perpendicular to the seven-fold axis of the pore. The top of the structure is on the cis side of the membrane in bilayer experiments. The 14-strand β barrel at the base of the structure opens the lipid bilayer. In the 4H subunit, residues Asn123, Thr125, Gly133, and Leu135 were replaced with histidine and Thr292 with cysteine. A close-up view of the antiparallel β strands that contribute to the lower part of the barrel is shown in FIG. 1E below.
Figure 1D:
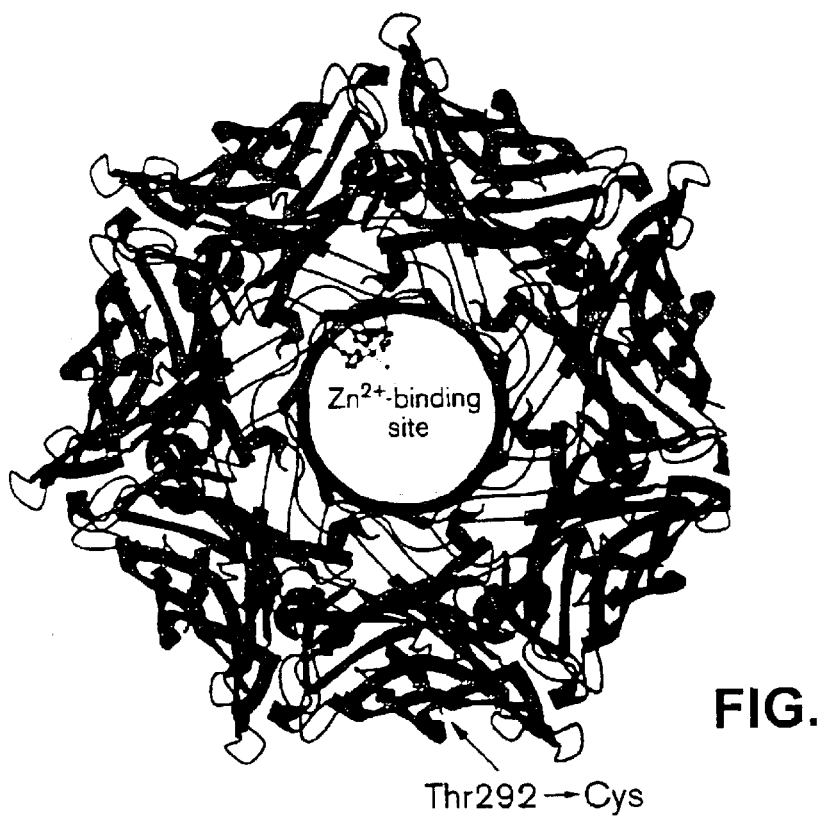
FIG. 1D is a diagram of the structure of a heteromeric αHL pore WT$_5$4H$_1$) assembly showing a Zn(II) binding site with a view of the heptamer down the seven-fold axis from the top (cis side of the pore. The four heterologous histidinyl residues project into the lumen of the channel, while Cys292 is distant from the channel mouth.
Figure 1E:
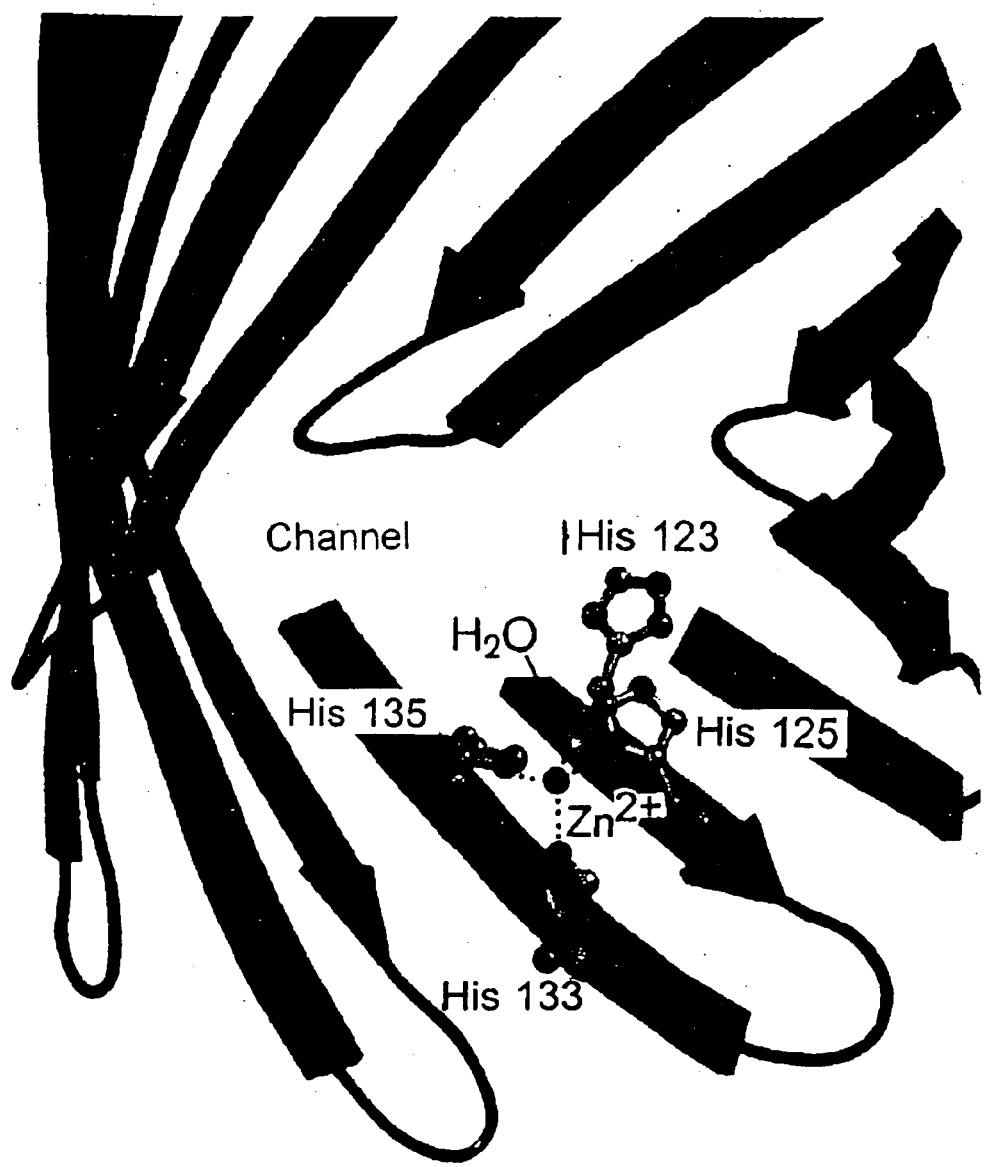
FIG. 1E is a diagram of the structure of the transmembrane channel portion of a heteromeric αHL pore assembly containing the Zn(II)-responsive αHL polypeptide 4H. Zn(II) is shown bound to the polypeptide at a binding site created by a heterologous metal-binding amino acid substitution.
Figure 1F:
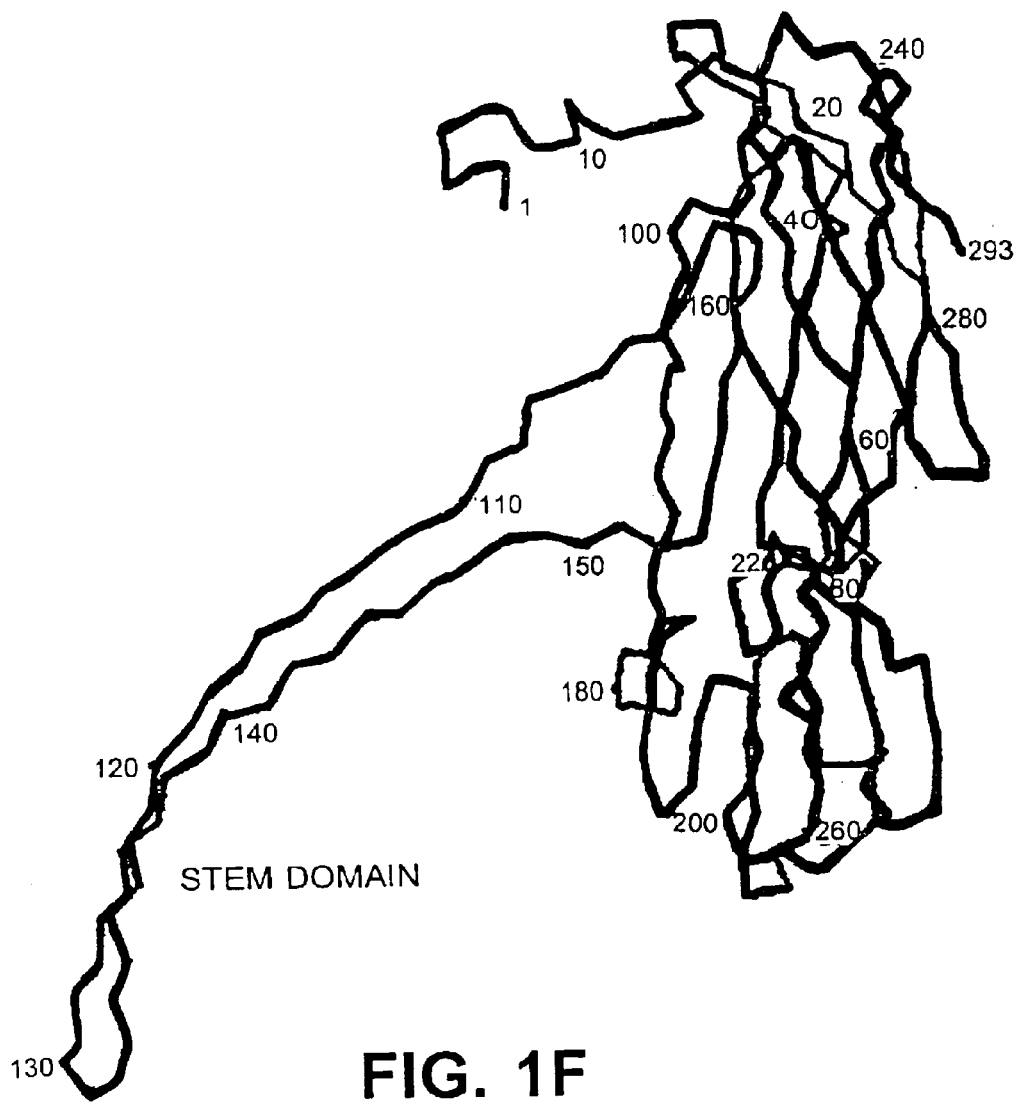
FIG. 1F is a diagram of the structure of an αHL polypeptide showing the stem domain spanning approximately amino acids 110–150.

Analyte-responsive αHL Polypeptides as Components of Biosensors

Biosensors generally have three elements: a) a binding site to recognize a target analyte (e.g., introduced by engineering metal-binding amino acids into an αHL polypeptide to create a metal binding site in the transmembrane channel of an αHL pore assembly), b) a transduction mechanism that signals the fractional occupancy of the binding site by the analyte (e.g., salt ions flowing through the αHL core assembly/channel at a rate of 100 million/sec for the open channel compared to an altered rates when an analyte is bound), and c) a method of measurement (and processing) of the transduction signal (e.g., pA, electrical measurements of the ion flux through the αHL pore assembly/channel in a membrane separating two liquid phases).

The compositions, devices and methods described herein can be used to track diverse analytes of interest in spatio-temporal gradients in water, in sediments and in the air. Such a capability would permit, for example, gradiometer-directed locomotion of robots. Other uses include detection, identification, and quantification of analytes in the environment, e.g., Cu, Zn, or Ni in effluents from underwater and dry dock hull cleaning operations, in shipboard waste processing, and in ocean micronutrient analyses.

Biosensors which incorporate protein pores as sensing components have several advantages over existing biosensors. In particular, bacterial pore-forming proteins, e.g.; αHL, which are relatively robust molecules, offer all the advantages of protein-based receptor sites together with an information-rich signal obtained by single-channel recording.

αHL is a 293 amino acid polypeptide secreted by *Staphylococcus aureus* as a water-soluble monomer that assembles into lipid bilayers to form a heptameric pore. The heptamer is stable in sodium dodecyl sulfate (SDS) at up to 65° C. The biophysical properties of αHL altered in the central glycine-rich sequence, by mutagenesis or targeted chemical modification, demonstrate that this part of the molecule penetrates the lipid bilayer and lines the lumen of the transmembrane channel. The channel through the heptamer is a 14-strand β barrel with two strands per subunit contributed by the central stem domain sequence (spanning approximately amino acids 110–150 of SEQ ID NO:1).

Table 1: WT αHL Amino Acid Sequence

ADSDINIKTG TTDIGSNTTV KTGDLVTYDK ENG-
MHKKVFY SFIDDKNHNK KLLVIRTKGT
IAGQYRVYSE EGANKSGLAW PSAFKVQLQL
PDNEVAQISD YYPRNSIDTK EYMSTLTYGF
NGNVTGDDTG KIGCLIGANV SIGHTLKYVQ
PDFKTILESP TDKKVGWKVI FNNMVNQNWG
PYDRDSWNPV YGNQLFMKTR NGSMKAADNFL
DPNKASSLL SSGFSPDFAT VITMDRKASK QQT-
NIDVIYE RVRDDYQLHW TSTNWKGTNT KDK-
WTDRSSE RYKIDWEKEE MTN (SEQ ID NO:1)

There is a need for biosensors that can detect a variety of analytes, ranging from simple ions to complex compounds and even microorganisms. Protein pores made from αHL polypeptides have been remodeled so that their transmembrane conductances are modulated by the association of analyses, e.g., divalent metal ions, M(II)s. The lumen of the transmembrane channel was altered to form different analyte-binding sites by design, e.g., by using site-directed mutagenesis to insert heterologous metal-binding amino acids. An analyte-binding αHL polypeptide is one that contains an engineered analyte-binding site not present in the WT αHL polypeptide. An analyte-binding site can be created by the introduction of as few as one heterologous analyte-binding amino acid, i.e., native residues may participate in forming a binding site. M(II)-binding sites can also be formed by the attachment of chelating molecules by targeted chemical modification. Combinatorial assembly is another way to generate diversity (see FIG. 2A). M(II) detection is rapid (e.g., single channel conductance is approximately $10^8$ ions sec$^{-1}$), reversible and sensitive. With digital single-channel recording for analyte detection, the binding sites need not be fully selective because the kinetics, extent and voltage-dependence of channel block provide a distinctive analyte signature. The voltage is gateable to further tune the biosensor. More than one analyte can be assayed simultaneously using the compositions and biosensor devices described herein. Selectivity is not a problem because a single analyte binding site can only be occupied by a single analyte at one time. Analyte-responsive αHL pores have been successfully used to detect an analyte of interest, e.g., a metal ion, in a solution containing a mixture of analytes as well as in solutions containing various concentrations of a single analyte.

Digital/Stochastic Single Channel Biosensors Using Analyte-Responsive αHL Polypeptides The attainment of sensitivity and selectivity is a major problem with most known biosensors as they are based on an integrated signal from numerous sensor molecules. The resulting signal is analogue/steady state and contains limited information about analyte identity(ies) and concentration(s). Analogue/steady state detection data is extremely difficult to extract reliably, even by modern processing hardware and software. For example, simultaneous competition for an analyte-binding site by many different analytes is a major problem. This problem is solved by the analyte-responsive αHL pores described herein.

The disclosed analyte-responsive αHL compositions are unique. A biosensor using an analyte-responsive αHL as the sensing component is tunable to any analyte target of interest by introducing an analyte-binding site directly into a measurable channel. Biosensors which incorporate an analyte-responsive αHL pore assembly reliably detect analytes in single channel mode, i.e., an individual analyte is detected as it randomly (stochastically) hops on and off a single binding site. These events are detected as modifications or perturbations of the ion conductance in the single channel.

A digital/stochastic biosensor device incorporating an αHL pore assembly as a sensing component has several important advantages over analogue/steady state biosensors. For example, the quality of the digital signal is independent of site occupancy; therefore, the dynamic range is orders of magnitude greater. Also, rate and equilibrium constants are read directly from the averages of a few spikes providing fundamental signature information about analyte identity and concentration. Simultaneous occupancy of a single binding site by different analytes cannot occur. Instead, competing analytes appear separated in time on the signal trace, each with it's own characteristic current signature.

FIG. 1A shows the interpretation of a digital/stochastic response of a single channel (patch clamp) recording using an analyte-responsive αHL pore assembly (FIGS. 6A–B show an expanded view of a recording). Digital detection reports stochastic behavior of a single analyte in real chemical time. The dynamic range of a biosensor incorporating an analyte-responsive αHL pore assembly is greater than 10,0000 fold compared to approximately 20 fold for other known biosensors.

Structure-based design and a separation method that employs targeted chemical modification have been used to obtain a heteromeric form of the bacterial pore-forming protein α-HL, in which at least one of the seven subunits contains a binding site for a divalent metal ion, M(II), which serves as a prototypic analyte. The single-channel current of the heteromer in planar bilayers is also modulated by nanomolar Zn(II). Other M(II)s (e.g., Co, Cu, Ni, and Cd) modulate the current and produce characteristic signatures. In addition, heteromers containing more than one mutant subunit exhibit distinct responses to M(II)s. Analyte-responsive αHL pores were generated through subunit diversity and combinatorial assembly.

Sensor arrays with components with overlapping analyte specificity, i.e., pore assemblies made from αHL polypeptides which respond to a variety of analytes, e.g., metal ions, provide a yet more powerful means for the simultaneous determination of multiple analytes and to expand the dynamic range. By using the design principles disclosed herein, binding sites for diverse analytes, e.g., different metal ions, can be engineered into the lumen of the transmembrane channel of an heteromeric αHL pore assembly or near an entrance to the transmembrane channel, e.g., near the cis entrance of the channel. The digital/stochastic detection mode can be generalized to classes of proteins other than pore-forming proteins, e.g., receptors, antibodies, and enzymes, with attached fluorescent probes to monitor individual binding events using imaging technology directly analogous to single channel recording. For example, analyte binding and dissociation from an active site (e.g., naturally-occurring or re-engineered analyte-binding site) of a remodeled fluorescent-tagged antibody, lectin, or enzyme is detected using the detection methods described above to determine the presence and/or concentration of an antigen, carbohydrate moiety, or enzyme ligand, respectively.

The compositions and biosensor devices described herein offer sensitivity, speed, reversibility, a wide dynamic range, and selectivity in detecting and determining the identity and concentration of analytes such as metal ions. αHL pores, remodeled so that their transmembrane conductances are modulated by the association of specific analytes, make excellent components of biosensors.

Engineered pores have several advantages over existing biological components of biosensors, e.g., sensitivity is in the nanomolar range; analyte binding a rapid (diffusion limited in some cases) and reversible; strictly selective binding is not required because single-channel recordings are rich in information; and for a particular analyte, the dissociation rate constant, the extent of channel block and the voltage-dependence of these parameters are distinguishing. A single sensor element can, therefore, be used to quantitate more than one analyte at once. Furthermore, the biosensor is essentially reagentless and internally calibrated. The approach described herein can be generalized for additional analytes, e.g., small cations and anions, organic molecules, macromolecules and even entire bacteria or viruses, by introducing a binding site for any given analyte into a portion of the αHL polypeptide, e.g., the stem domain, which participated in forming the transmembrane channel of the αHL pore assembly. For example, a heterologous aromatic amino acid substitution can be engineered into an αHL polypeptide, e.g., in the transmembrane channel portion of an αHL pore assembly or at the mouth of the channel, to confer responsiveness to a variety of organic molecules. Furthermore, combinatorial pore assembly of metal-responsive αHL polypeptides and WT αHL polypeptides generate pores with diverse detection capabilities (see FIG. 2A).

An analyte-responsive αHL pore containing a subunit in which amino acids positions 123 and 125 of SEQ ID NO:1 were substituted with tryptophan (123W/135W) was made. This mutant αHL polypeptide was used to discern the presence and/or concentration of organic molecules. For example, 123W/125W binds the explosive TNT. Single-channel recordings using pore assemblies containing a 123W/125W subunit detected TNT (FIGS. 8A–B).

αHL Pore Assemblies

WT αHL pores are homomeric; that is, all seven subunits are the same. The analyte-responsive pores described herein may be homomeric or heteromeric and contain at least one mutated αHL polypeptide subunit. For example, a pore assembled from seven subunits has the formula $WT_{7-n}MUT_7$, where MUT is a mutant αHL polypeptide and where n=1, 2, 3, 4, 5, 6, or 7. Preferably, the MUT subunit is an analyte-binding αHL polypeptide. The amino acid sequence of MUT differs from that of WT in that MUT may be longer or shorter in length compared to the WT subunit (e.g., MUT may be truncated, contain internal deletions, contain amino acid insertions, or be elongated by the addition terminal amino acids, compared to the WT sequence); alternatively, MUT may contain one or more amino acid substitutions in the WT sequence (or MUT may differ from WT both in length and by virtue of amino acid sequence substitutions). The engineered changes in the MUT subunit preserve the ability of MUT co associate with other αHL polypeptides to form a pore structure.

A heteromeric pore was made that binds the prototypic analyte Zn(II) at a single site in the lumen of the transmembrane channel, thereby modulating the single-channel current. In addition, M(II)s other than Zn(II) modulate the current and produce characteristic signatures. Heteromers containing more than one mutant subunit exhibit distinct responses to M(II)s. The invention therefore provides an extensive collection of heteromeric responsive pores suitable as components for biosensors.

Molecular Modeling of αHL Pore Assemblies

The three-dimensional structure of an αHL pore assembly was determined using known methods, e.g., those described in Song et al., 1996, Science 274:1859–1865. Using the modeling techniques described below, the position of amino acids which occupy the transmembrane channel portion of an αHL pore assembly and/or protrude into the lumen of the transmembrane channel can be determined. For example, to analyze the structures of αHL polypeptides described herein, the coordinates of carbonic anhydrase 11 (Eriksson et al., 1986, Proteins: Struct. Funct. Genet. 4:283–293) were obtained (PDB accession number 1CA3). Two β strands (residues 91–98 and 116–121), containing the histidines that bind Zn(II), were isolated and fitted by a blast square procedure to the β strands in the stem of protomer A of the αHL structure (Song et al., 1996, Science 274:1859–1865). Residues 123–126 and 132–135 of αHL were then replaced with 117–120 and 93–96 of carbonic anhydrase. The αHL sidechains were substituted back into the structure, with the exception of the histidines at positions 123, 125, 133, and 135. The Zn(II) ion and the attached water molecule from carbonic anhydrase were left in place. In addition, Thr292 was replaced with a cysteine residue. The new molecule was drawn with Molscript (Kraulis, P. J., 1991, J. Appl. Cryst. 24:946–949) and a final version rendered with Raster3D (Merritt et al., 1994, Act Cryst. D50:869–873).

Mutagenesis

Recombinant αHL polypeptides, e.g., metal-responsive αHL polypeptides, were made using methods well known in the art of molecular biology. For example, the metal-responsive αHL polypeptide, 4H, was made using DNA encoding a full-length αHL (αHL-RL) that had been partly reconstructed from the native S. aureus αHL gene (Walker et al., 1992, J. Biol. Chem. 267: 10902–10909) with synthetic oligonucleotides to introduce unique restriction sites in the central region (residues 116–147). Four conservative amino acid replacements are present in αHL-RL: Val124→Leu, Gly130→Ser, Asn139→Gln and Ile142→Leu. The region encoding amino acids 118–138 was removed by digestion with BsiWI and ApaI and replaced with two synthetic duplexes (BsiWi-SpeI and SpeI-ApaI) encoding the replacements Asn123→3His, Val124→Leu, Thr125→His, Gly130→Ser, Gly133→His, Leu135→His. A 700 base pair fragment of the resulting construct, encompassing the four new histidines, was removed with NdeI and MfeI and used to replace the corresponding sequence in αHL-Thr292→Cys. The entire coding region of the resulting αHL-4H/Thr292→Cys construct was verified by sequence analysis.

Expression and Purification of αHL Polypeptides

Monomeric WT-αHL was purified from the supernatants of S. aureus cultures using known methods, e.g., the method described in Walker et al., 1992, J. Biol. Chem. 267: 10902–10909. [$^{35}$S]-Methionine-labeled WT-αHL and αHL-4H were obtained by coupled in vitro transcription and translation (IVTT). Separate reactions conducted with a complete amino acid premix and the premix without unlabeled methionine were mixed to yield a solution containing αHL at >10 μg/ml. αHL in the IVTT mix was partially purified by (i) treatment with 1% (w/v) polyethyleneimine (PEI) to precipitate nucleic acids, (ii) treatment with SP Sephadex C50, pH 8.0 (to remove the residual PEI), and (iii) binding to S-Sepharose Fast Flow at pH 5.2, followed by elution with 10 mM sodium acetate, pH 5.2, 800 mM NaCl. The concentration of αHL (in the IVTT mix or after the purification) was estimated by a standard quantitative hemolytic assay.

Oligomerization of αHL Polypeptides

WT and αHL-4H were mixed in various molar ratios (6:0, 5:1, 1:1, 1:5, and 0:6) and allowed to oligomerize on rabbit erythrocyte membranes, liposomes, and other planar bilayers. The αHL polypeptides self-assemble into heteroheptameric pore assemblies in bilayers. For rabbit erythrocytes membranes, oligomerization was carried out as follows. Mixtures were incubated for 1 h at room temperature in 10 mM MOPS, pH 7.4, 150 mM NaCl. The membrane were washed and resuspended in 200 mM TAPS, pH 9.5, treated with 0.5 mM DTT for 5 min and then with 10 mM 4-acetamido-4'-[(iodoacetyl)aminol stilbene-2.21-disulfonate (IASD, Molecular Probes, Eugene, Oreg., USA) for 1 h at room temperature to modify the Cys292 residue on the 4H polypeptide chain. The membranes were recovered by centrifugation, taken up in gel loading buffer, without heating, and loaded onto a 7W SDS-polyacrylamide gel (40 cm long, 1.5 mm thick). Electrophoresis was carried out for 16 h at 120 V at 4° C. with 0.1 mM thioglycolate in the cathode buffer. The dried gel was subjected to phosphorimacer or audioradiographic analysis.

Heteroheptamer Formation and Purification

Heteromeric pore assembly by αHL polypeptides in membranes and other planar bilayers suitable for use in biosensor devices was carried out using known methods, e.g., those described by Hanke et al., 1993, Planar Lipid Bilayers, Academic Press, London, UK; Gutfreund, H., 1995, Kinetics for the Life Sciences, Cambridge University Press, Cambridge, UK). Rugged planar bilayers are described in Cornell et al., 1997, Nature 387:580–583.

For example, to generate 4H heteroheptamers, unlabeled WT-αHL and $^{35}$S-labeled 4H were mixed in a 5:1 ratio (WT-αHL; 2.5 μl of 0.5 mg/ml in 20 mM sodium acetate, pF 5.2, 150 mM NaCl; $^{35}$S-labeled 4H; 50 μl of 5 μg/ml). The mixed subunits were allowed to oligomerize on liposomes for 60 min at room temperature by incubation with 10 mM MOPS, pH 7.4, 150 mM NaCl (26 μl) and egg yolk phosphatidylcholine (Avanti Polar Lipide, Birmingham, Ala., USA; 1.5 μl of 10 mg/ml). The latter had been bathed sonicated at room temperature until clear (30 min) in 10 mM MOPS, pH 7.4, 160 mM NaCl. The mixture (60 μl) was then treated with 2 M TAPS, pH 8.5 (10 μl), and 10 mM DTT (6 μl) for 10 min at room temperature, followed by 100 mM IASD (5 μl in water) for 60 min at room temperature. Gel loading buffer (5×, 25 μl) was then added, without heating, and a portion (50 μl) was loaded into an 8 mm wide lane of a 40 cm long, 1.5 mm thick 6% SDS-polyacrylamide gel, which was run at 4° C. at 120 V for 16 h, with 0.1 M thioglycolate in the cathode buffer. The unfixed gel was vacuum dried without heating onto Whatman 3MM chromatography paper (#3030917).

Each of the eight heptamer bands was cut from the gel, using an autoradiogram as a guide. The excised pieces were rehydrated with water (100 μl). After removal of the paper, each gel strip was thoroughly crushed in the water and the protein was allowed to elute over 18 h at 4° C. The solvable eluted protein was separated from the gel by centrifugation through a 0.2 μm cellulose acetate filter (#7016-024, Rainin, Woburn, Mass., USA). A portion (20 μl) was saved for single channel studies. Sample buffer (5×, 20 μl) was added to the rest of each sample. Half was analyzed, without heating, in a 40 cm long 8% SDS-polyacrylamide gel. The other half was dissociated at 95° C. for 5 min for analysis of the monomer composition in a 10% gel.

Biosensor: Planar Bilayer Recordings

Detection of analytes using heteroheptameric αHL pore assemblies in planar bilayers was carried out as follows. A bilayer of 1,2-diphytanoyl-sn-glycerophosphocholine (Avanti Polar Lipids) was formed on a 100–200 μm orifice in a 25 μm thick teflon film (Goodfellow Corporation, Malvern, Pa., USA), using standard methods, e.g., the method of Montal and Mueller (Montal et al., 1972, Proc. Natl. Acad. Sci. USA 69:3561–3566). Both chambers of the device contained 1 M NaCl, 50 mM MOPS, pH 7.5, and other solutes as described in the figure legends. Two to 10 μl of the eluted protein were added to the cis chamber to a final concentration of 0.01–0.1 ng/ml. The bilayer was held at −10 mV with respect to the trans side. The solution was stirred until a channel inserted. The analyte Zn(II) was added with stirring, to the trans chamber from a stock solution of 100 mm $ZnSO_4$ in water. Where Zn(II) was buffered, the concentration of free Zn(II) was calculated using the program Alex (Vivadou et al, 1981, J. Membrane Biol. 122:155–175). Currents were recorded by using a patch clamp amplifier (Dagan 3900A with the 3910 Expander module), filtered at 5 kHz (four-pole Internal Bessel filter) and stored with a digital audio tape recorder (DAS-75; Dagan Corporation, Minneapolis, Minn., USA). For example, the data were filtered at 1–2 kHz (eight-pole Bessel filter, Model 900, Frequency Devices) and acquired at 5 kHz onto a personal computer with a Digidata 1200 D/A board (Axon Instruments). The traces were filtered at 100–200 Hz for display and analysis with the Fetchan and pSTAT programs, both of pCLAMP 6. Negative current [downward deflection] represents positive charge moving from the cis to the trans chamber.

Molecular Design of Heteromeric αHL Pores

A Zn(II)-binding αHL polypeptide was made by substituting one or more amino acids in the stem domain of WT αHL with a heterologous metal-binding amino acid. One example of such a Zn(II)-binding polypeptide is 4H which contains the following amino acid substitutions in the stem domain of αHL: Asn123→His, Thr125→His, Gly133→His, Leu135→His, Thr292→Cys. Four histidines were introduced by mutagenesis co project into the lumen of the channel (e.g., at odd numbered positions of the stem domain) to form a cluster of imidazole sidechains. αHL polypeptides in which heterologous metal-binding amino acids have been introduced such that they are located on the outside of the barrel (e.g., at even numbered positions of the stem domain) of the pore assembly also confer responsiveness to metal ions. In addition, amino acid substitutions in regions of the αHL polypeptide outside the stem domain but which are close to the lumen of the transmembrane channel, e.g., at the mouth of the channel, also confer metal responsiveness.

The channel through the heptamer is a 14-strand β barrel with two strands per subunit (see FIGS. 1C–F) contributed by the central stem domain sequence which spans approximately amino acids 110–150 of SEQ ID NO:1: EYMSTL-TYGF NGNVTGDDTG KIGGLIGANV SIGHTLKYVQ (SEQ ID NO:2). Structural data indicates that the β barrel is sufficiently flexible for at least three sidechains to act as ligands to Zn(II) in the preferred tetrahedral configuration.

To facilitate separation of polypeptides, the 4H polypeptide was also cogged by chemical modification of the single cysteine (at position 292) with 4-acetamido-4'-[(iodoacety) amino]stilbene-Z,Z'-disulfonate (IASD). The Cys-cogged αHL (Thr292o→s; without amino acid substitutions in the stem domain) modified with IASD forms fully active homomers. This modification caused an incremental increase in the electrophoretic mobility of heptamers in SDS-polyacrylamide gels allowing heteromers to be easily separated from each other and from wild-type (WT) heptamers. Each disulfonate made an approximately equal contribution to the mobility, which is independent of the arrangement of the subunits about the seven-fold axis. The chemical modification was distant from the stem domain of the polypeptide which lines the channel of the heteromeric pore assembly.

Assembly and Separation of αHL Metal-responsive Heteromeric Pores

Figures 2A, 2B:
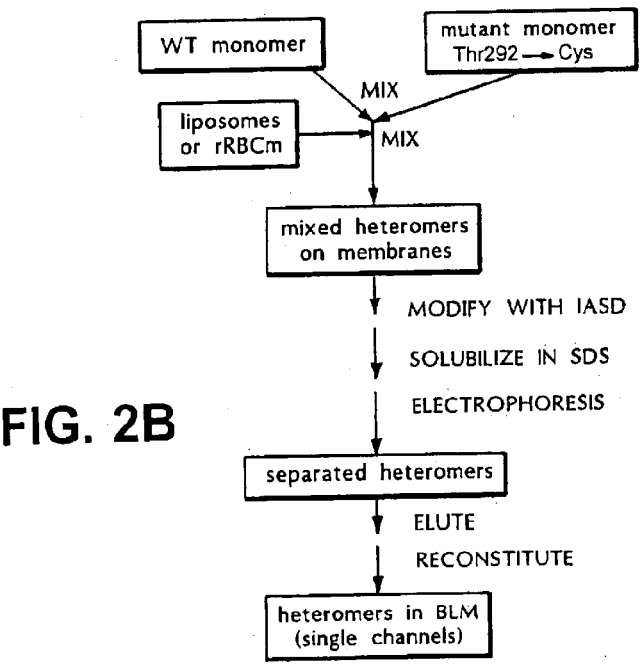
FIG. 2A is a diagram of heteromeric combinations resulting from the assembly of mixtures of wild-type (WT) and mutant (MUT) αHL monomers showing the assembly of heteromeric αHL pores. The 20 different heteromers (WT$_{n-m}$MUT$_m$; n=7, the total number of subunits; WT, open circles; mutant, closed circles) fall into n+1 classes categorized by the number of mutant subunits (m) in the heptamer. The proportions of heptamers (%) in each class is shown for three starting ratios of monomers (WT:MUT, 5:1; 1:1; 1:5). The values were calculated assuming that the oligomerization process does not distinguish between WT and MUT monomers, by using 100.P$_m$=100. [n!/m!(n−m!)]. f$_{MUT}^m$·f$_{WT}^{n-m}$, where f$_{MUT}$ and f$_{WT}$ are the fractions of mutant and WT subunits, respectively, in the starting monomer mix.
FIG. 2B is a diagram showing the procedure for assembly and separation of heteroheptameric αHL pore assembly. Heteromers were formed from the desired ratio of WT and MUT subunits on either rabbit red blood cell membranes (rRBCM) or liposomes. The heteromers were then derivatized with IASD, which introduced two negative charges for each mutant (Cys292-containing) subunit. The eight classes of heptomer were then separated by SDS-polyacrylamide gel electrophoresis (SDS-PAGE). The members of a particular class were obtained by elution from the polyacrylamide.
Figure 2C:
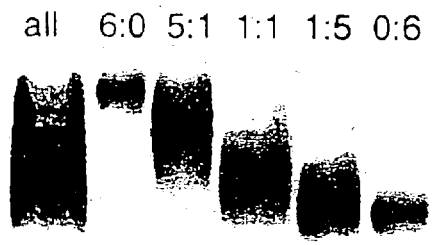
FIG. 2C is a photograph of an electrophoretic gel showing separation of different classes of α heptamers. WT αHL and the mutant 4H, both [$^{35}$S]-labeled, were mixed in the ratios indicated, allowed to assemble on rRBCM and then treated as shown in FIG. 2B. The membranes were solubilized in gel loading buffer containing SDS and, without heating, subjected to electrophoresis in a 7% gel. A phosphorimager display of the molecules migrating near the 200 kDa marker (myosin heavy chain) is shown. The observed ratios of oligomer classes seen in each lane approximate those shown in FIG. 2A. The lane marked "All" contained a mixture of the solubilized samples at all five WT:4H ratios.
Figure 3B:
FIG. 3B is an electrophoretic gel showing that WT$_7$ and 4H$_7$ did rot become scrambled under the conditions used for extraction, storage and reconstitution. An excised WT$_7$ band was mixed and coeluted with an excised 4H$_7$ band. The sample was kept at 4° C. for 24 h and then stored at −20° C. The thawed sample was run on a 40 cm long 8% SDS polyacrylamide gel. The bands retained their integrity (i.e. there is no ladder of species to suggest subunit interchange).
Figure 3A:
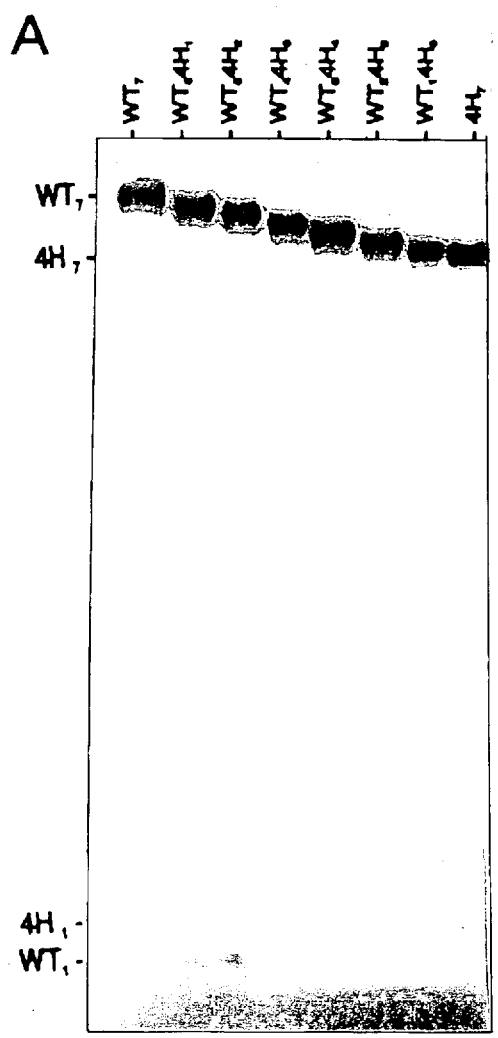
FIG. 3A is a photograph of an electrophoretic gel showing purified αHL heteroheptamers. Heptamers were stable in SDS and the subunits did not interchange. All eight radiolabeled WT$_{n-m}$4H$_m$ heptamers were purified by SDS-PAGE, rerun on a 40 cm long 8% SDS-polyacrylamide gel and visualized by autoradiography. The individual heteromer species (lanes 1–8) retained their relative mobilities, resulting in the staircase appearance of the image.

There is only one possible arrangement of heteromers containing six WT and one 4H subunit ($WT_6 4H_1$; FIG. 2A). Therefore, the $WT_6 4H_1$ pore assembly is consistently and reliably formed. The 4H mutant of αHL was prepared using known methods for making recombinant proteins, e.g., in vitro transcription and translation (IVTT). In some cases, αHL was radiolabeled with [$^{35}$S]methionine. WT αHL was also prepared by IVTT when labeling was desired. Alternatively, WT αHL was purified from S. aureus. WT and 4H were mixed in a molar ratio of 5:1 and allowed to assemble on lipid bilayers, e.g., rabbit red blood cell membranes (rRBCM) or on liposomes made from egg yolk phosphatidylcholine (FIG. 2B). After assembly, the 4H subunits were modified at Cys292 with IASD. The membranes were solubilized in SDS and the heteromers separate by SDS-polyacrylamide gel electrophoresis (SDS-PAGE; FIG. 2C). Heptamers were eluted passively from the polyacrylamide with water, for reconstitution into bilayers for biophysical characterization. The eluted heteromers remained intact as shown by re-electrophoresis (FIG. 3A). These data demonstrated that the polypeptides did not become scrambled, thus indicating the predictability of pore assembly. For example, $WT_7$, and $WT_54H_2$ were not formed from $WT_64H_1$.

Figure 4A:
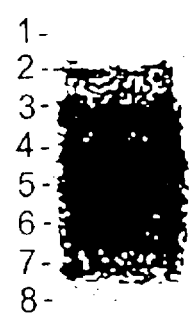
FIG. 4A is an autoradiogram of the SDS-PAGE separation of approximately 5:1 mixture of WT and 4H, from which WT$_6$4H$_1$ was eluted and used for single channel studies. Unlabeled WT was used, so the first detectable band is WT$_6$4H$_1$. This band appears relatively weak here because it contains a single $^{35}$S-labeled 4H subunit.
Figure 3C:
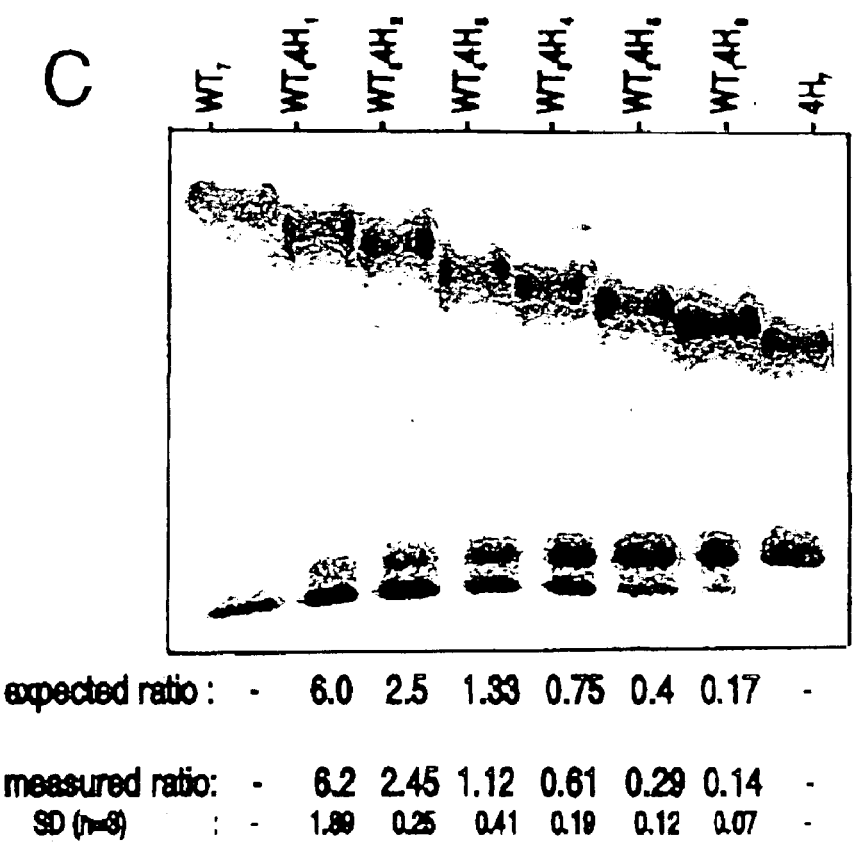
FIG. 3C is a photograph of an electrophoretic gel showing the ratio of the WT and 4H subunits in each purified heptamer. Heptamers were made as described in the legend to FIG. 3A. Half of each sample was subjected to electrophoresis without heating (top panel), while the other half was dissociated by heating to 95° C. (bottom panel). The mutant αHL monomers, modified with IASD, were separated from the more rapidly migrating WT polypeptides in a 40 cm long 10% SDS-polyacrylamide gel, allowing the quantitation of the two monomer species contained in each heptamer by phosphorimager analysis (ImageQuant, Molecular Dynamics). The expected and measured ratios are shown below each lane.

In two out of five such runs, small amounts of monomer (<5%) were detected. Such breakdown was probably due co the storage conditions that the two samples experienced (e.g. for the sample displayed in FIG. 3A, several freeze/thaw cycles, followed by storage at 4° C. for ten days). In the other three runs, where freshly eluted heptamers were examined, monomers were nor detected at all. In a definitive experiment, gel slices containing the homomers $WT_7$ and IASD-modified $4H_7$ were mixed and taken through the elution and storage procedures before re-electrophoresis, which again indicated no scrambling (FIG. 3B). Furthermore, the eluted heptamers were free of residual proteins from the IVTT mix, as determined by silver staining. Finally the ratio of the αHL polypeptides in each of the heteromeric pore assemblies examined was as expected, when determined by quantitative analysis of radio-labeled polypeptides from purified heteromers dissociated by heating to 95° C. (FIG. 3C). The electrophoretic gel shown in FIG. 4A confirms the heteromeric channel structure of the αHL pore assembly.

Digital Single-channel Currents from Heteromeric Metal-responsive Pores

The properties of $WT_64H_1$ were examined by digital single-channel recording in a planar bilayer biosensing apparatus. Methods for forming planar bilayers in biosensors are known in the art, e.g., Hanke et al., 1993, Planar Lipid Bilayers, Academic Press, London, UK or Gutfreund, H., 1995, Kinetics for the Life Sciences, Cambridge University Press, Cambridge, UK. In this experiment, a lipid bilayer was formed across an aperture (100–200 μm diameter) in a teflon film (25 μm thick) that separates two chambers (2 ml each) containing electrolyte. With a potential applied across the bilayer, the ion flux through single αHL pores was measured with a sensitive, low-noise amplifier.

Figure 4B:
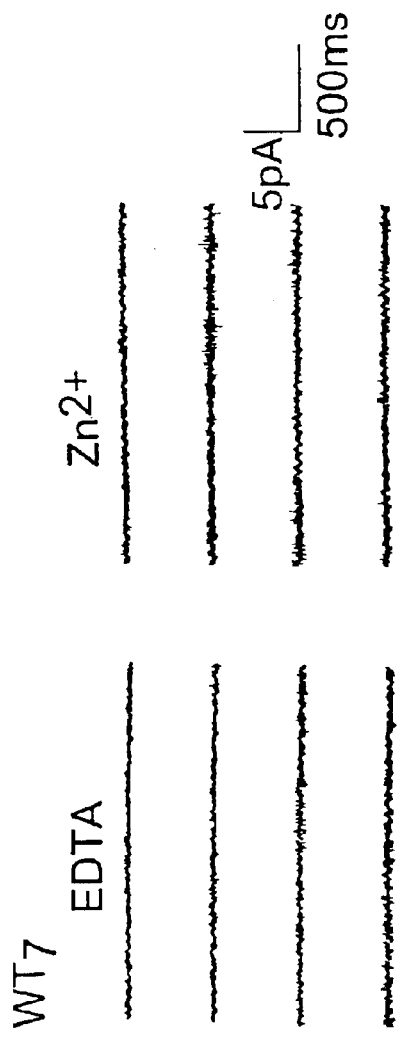
FIGS. 4B, 4C, and 4D are a series of graphs of digital single-channel recordings from a heteromeric αHL channel containing a Zn(II) binding site. Single-channel recordings were made using purified WT$_7$ and WT$_6$4H$_1$ pore assemblies in planar lipid bilayers. Both cis and trans chambers of the device contained 1 M NaCl, 50 mM MOPS, pH 7.5. Four consecutive traces of a single-channel current at −40 mV are shown for each species. Left, currents in the presence of 100 μM EDTA; right, currents after the addition of 150 μM ZnSO, to the trans side of the membrane (approximately 50 μM free Zn(II)).
Figure 4C:
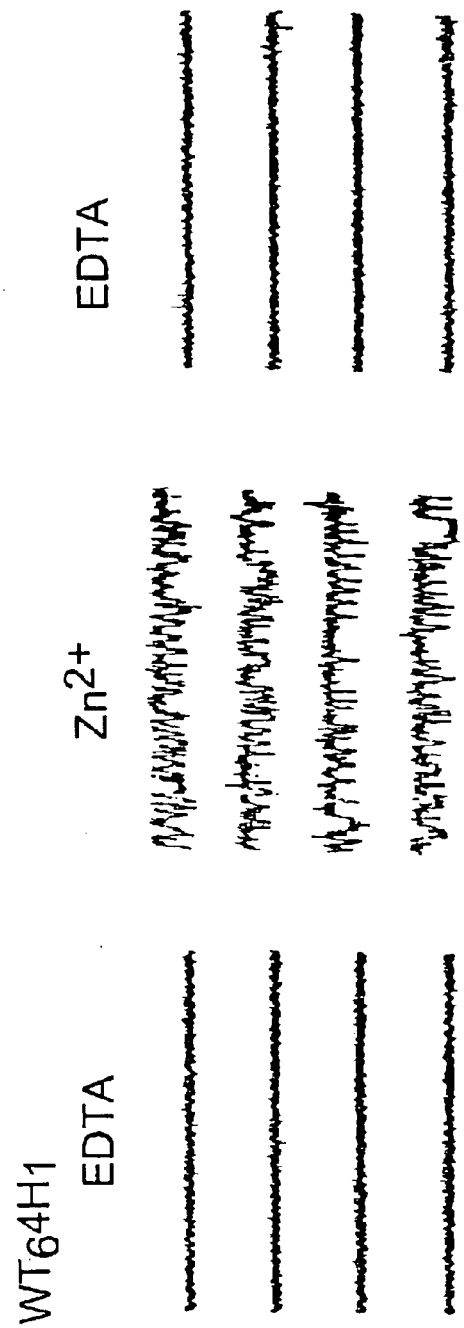
Figure 4D:
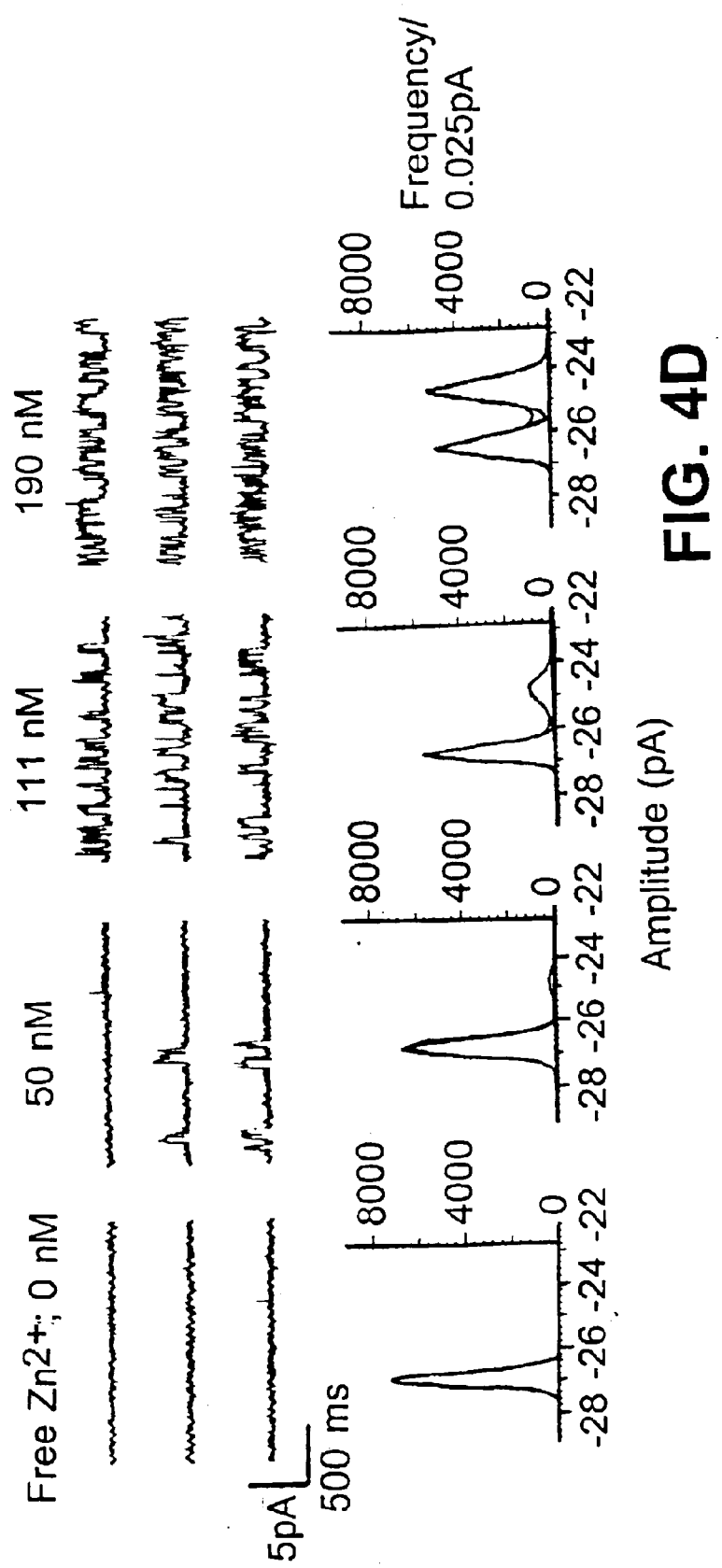

To obtain single-channel currents, the eluted heptamers were added at high dilution (typically 1:1000) to the cis chamber of the bilayer apparatus to a final concentration of 0.02–0.1 ng/ml (FIGS. 4B–D). $WT_64H_1$ exhibited a partial and reversible channel block ($g/g_0$-0.93±0.01$_1$; n=7) in the presence of 50 μM Zn(II) in the trans compartment with the transmembrane potential held at −40 mV (FIG. 4C).

The behavior of heteromeric $WT_64H_1$ pores were compared to two different control pores. $WT_7$ control pores were not sensitive under the conditions described above (see FIG. 4B) and were unaffected by up to 500 μM Zn(II). Heteromeric $WT_64H_1$ pores were also compared to control pores made with $wT_64H_1$ with an additional Thr292→Cyr mutation, modified with IASD. This heptamer also gave no response with Zn(II). FIG. 4B shows data from $WT_7$ αHL pore assemblies (i.e., control pores); control pores did not respond to the presence of Zn(II) or EDTA (a chelating agent that complexes M(II)).

Analysis of conductance histograms for $wT_64H_1$ obtained for a series of buffered Zn(II) concentrations (FIG. 4D) yielded an $EC_{50}$ for trans Zn(II) of 112±23 nM (n=3). The $EC_{50}$ is the concentration of free M(II) that effects 50% occupancy of the binding site of 4H. Kinetic analysis of the current traces yielded a second-order associated rate constant ($k_{on}$) for Zn(II) of $3.2±0.4×10^8 M^{-1}s^{-1}$ (n=4) which approaches the diffusion limit, and a dissociation rate constant ($k_{off}$) of $33±2s^{-1}$ (n=4). The $EC_{50}$ value was lower than expected for two histidinyl ligands and approached the values found for structures with three histidines with favorable geometry (e.g. 36 nM for a mutated retinol-binding protein), suggesting that a modest distortion of the β barrel can be tolerated that places at least three of the four histidines in conformations suitable for coordination of the bound metal. The flexibility of the barrel is supported by (1) the three-dimensional structure of αHL, (2) the fact that for αHL in liposomes blue shifts of the fluorescent probe acrylodan (attached at single cysteine residues in the α barrel) do not alternate with residue number (as would be required for nondistorted β strands), and (3) the existence of mutants with proline residues in the central domain that form pores.

The conductance of $WT_7$ pores (675±62pS$_1$ 1M N$_a$Cl$^1$ 50 mM MOPS, pH7.5$_1$-40 mV, n=8) was similar to that of $WT_64H_1$ in the absence of Zn(II) (660±40pS$_1$ n=7). The conductance of $WT_64H_1$ with Zn(II) bound was reduced to 610±45 pS (n=7). A partial channel block may be due to a simple physical blockade, distortion of the barrel, or electrostatic effects.

FIGS. 4C and 4D show digital responses of the engineered $WT_64H_1$ hybrid channel to various levels of Zn(II). The digital pattern is due to the stochastic (random) effect of single zinc ions hopping on and off the tetra-histidyl binding site engineered into the lumen of the transmembrane channel of an αHL pore assembly. The two channel states are open (Zn(II) off, 100% open) and gated (Zn(II) on, 93% open). Average time in the open state is the reciprocal of bimolecular rate constant×(Zn(II)], from which Zn(II) is quantified, while average time in the gated state is the reciprocal of the first order off constant (the analyte signature or identity). Monovalent metal cations gave no signal. These data indicate that the metal-responsive αHL polypeptides and pore assemblies used as components of a biosensor provide a means to achieve unambiguous analyte identity and concentration(s). Existing chemo/bio-sensors are analog/steady state, whereas the channel of the αHL pore assembly is digital/stochastic. FIG. 4 also shows that αHL pore assemblies have an wide dynamic range of analyte detection (at least 10,000-fold in analyte concentration. Even at very low fractional site occupancies, the signal (being digital and not analog) is not degraded. At very low site occupancy, it simply may take longer to collect to collect data (however, sensitivity and selectivity is not compromised).

Figure 5A:
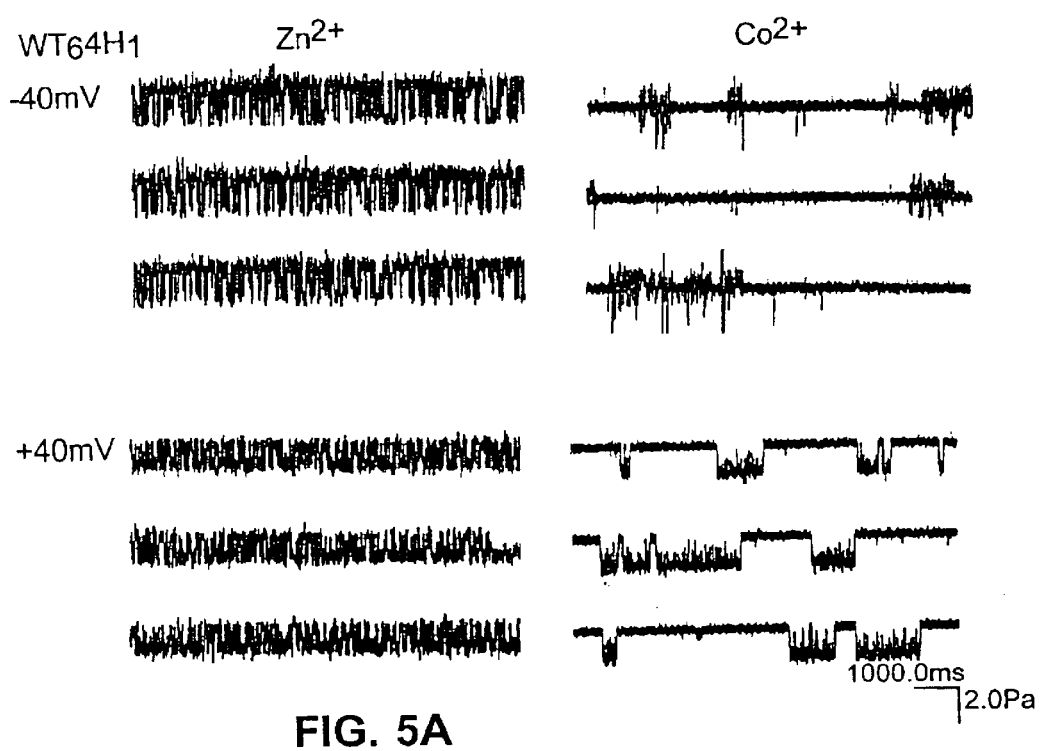
FIG. 5A is a series of graphs of digital single channel recordings from $WT_6 4H_1$ in the presence of 5 µM free Zn(II) or 5 µM free Co(II) showing response of the heteromeric pores to different M(II)s and tuning of the sensitivity to M(II)s by adjustment of subunit composition. Top, transmembrane potential −40 MV; bottom, transmembrane potential +40 mV.

Metal-responsive αHL Pores Produce Characteristic Single-channel Signatures in Response to Various Divalent Metal Cations To determine whether $WT_64H_1$ can distinguish between different M(II)s, the effects of Co(II), Ni(II) and Cu(II) on single-channel currents were examined. Each gave a characteristic current signature. For example, at −40 mV 5 μM, Co(II) produced a distinctive current signature compared to, e.g., Zn(II) (FIG. 5A, top). At higher Co(II) concentrations, the signal was continuous resulting from the rapid interconversion of three states, one with higher conductance than $WT_64H_1$ in the absence of M(II). At +40 mV, two states were seen with 5 μM Co(II) (FIG. 5A, bottom). The effect on current amplitude is similar to that of Zn(II) at this membrane potential, but the rates of Co(II) association and dissociation are considerably slower. These data also show that the responses of single-channel currents to membrane potential contain additional information about the concentration and identity of analytes.

Figure 5B:
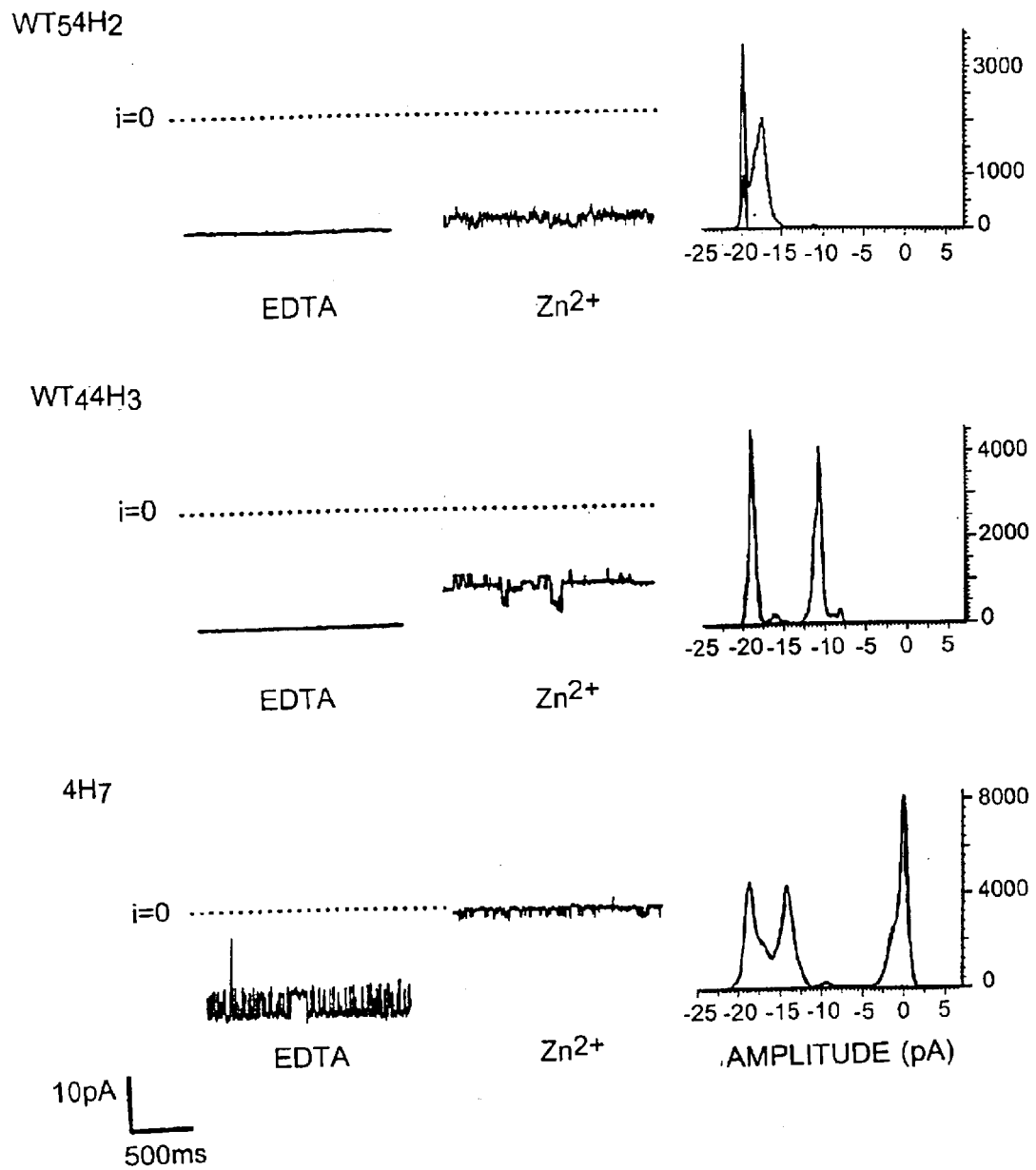
FIG. 5B is a series of graphs showing the response of pores containing more than one 4H subunit to Zn(II). $WT_5 4H_2$ (concentration of free Zn(II)=50 µM), $WT_7 4H_1$ (20 µM) and $4H_7$ (10 µM). Left, digital single channel recordings of currents in the absence (EDTA) and presence of Zn(II). The zero current level is indicated (i=o). Right, the corresponding all points histograms (light line, EDTA; dark line, Zn(II)).
Figure 7A:
FIGS. 7A and 7B are graphs of digital single channel recordings from $WT_6 4H_1$ in the presence of a solution containing 40 nM Zn(II) and 40 nM Ni(II) at a transmembrane potential of −40 MV.
Figure 7B:

The data in FIG. 5A indicate that different M(II) give different digital output patterns, i.e., spikes from one M(II), e.g., Zn(II), are not hidden under the spikes of another, e.g., Co(II), because only one metal ion can occupy a single site at one time. In a complex mixture of analytes, deconstruction of the signal is required to isolate the current signature of an analyte of interest. The sensitivity and precision of analyte identification achieved by the compositions and digital/stochastic devices of the invention vastly exceed those achieved by known analogue/steady state biosensor devices. For example, simultaneous competitive inhibition owing to incomplete selectivity is a universal problem with conventional chemo/bio-sensors, requiring extensive downstream processing. In contrast, the identity and concentration of analytes can easily, reliably, and accurately determined from traces such as those in FIGS. 4A–D and 5A–B, i.e., analytes can be identified (as well as quantified) by the single-channel current signature ($\Delta g$, $k_{on}$, $k_{off}$, voltage dependence of these parameters). FIG. 5 also illustrates that the channel can further be tuned by changing the transmembrane voltage. FIGS. 7A–B show that digital output patterns corresponding to different analytes allow the detection and quantification of analytes, e.g., Zn (II) and Ni (II), even in solutions containing a mixture of analytes. These data indicate that αHL biosensors may be used to detect, identify, and quantify analytes in complex mixtures, e.g., environmental samples or waste water samples.

Additional 4H Heteromers Exhibit Different Responses to Divalent Cations

Structural variants of αHL pores resulting from combinatorial assembly provide yet another means by which to tune an αHL channel for detection of analytes. In addition to the experiments described above, other combinations of $WT_{7-n}4H_n$ were tested. The extent of single-channel block by Zn(II) increased with the number of 4H subunits. Multiple subconductance states were observed as exemplified by the data for $WT_54H_2$, $WT_44H_3$, and $4H_7$ (FIG. 5B). The specific permutations of the $WT_54H_2$ and $WT_44H_3$ pores in these recordings was not determined, however single-channel recording actually provides a means to "separate" the various permutations of each combination of heteromers. According to these data, combinatorial assembly can provide pores with characteristic responses over a wide range of analyte concentrations.

Other embodiments are within the following claims.

What is claimed is:

1. A staphylococcal alpha hemolysin (αHL) polypeptide comprising at least two non-consecutive heterologous amino acids in a stem domain of said polypeptide, wherein each of said heterologous amino acids binds a metal.

2. The polypeptide of claim 1, wherein said amino acids occupy two or more of the following positions of SEQ ID NO: 1: 111, 113, 115, 117, 119, 121, 123, 125, 127, 129, 131, 133, 135, 137, 139, 141, 143, 145, 147 or 149.

3. The polypeptide of claim 1, wherein said amino acids occupy two or more of the following positions of SEQ ID NO: 1: 110, 112, 114, 116, 118, 120, 122, 124, 126, 128, 130, 132, 134, 136, 138, 140, 142, 144, 146, 148.

4. The polypeptide of claim 1, wherein said polypeptide comprises at least three non-consecutive heterologous amino acids in the stem domain of said polypeptide.

5. The polypeptide of claim 1, wherein said polypeptide comprises at least 4 non-consecutive heterologous amino acids in the stem domain of said polypeptide.

6. The polypeptide of claim 5, wherein said amino acids occupy positions 123, 125, 133, and 135 of SEQ ID NO: 1.

7. The polypeptide of claim 6, wherein said polypeptide is 4H.

8. A mutant staphylococcal alpha hemolysin polypeptide comprising a heterologous amino acid, wherein the heterologous amino acid binds an analyte and wherein the polypeptide assembles into a heteroheptameric pore assembly in the presence of a plurality of wild type staphylococcal alpha hemolysin polypeptides and wherein the amino acid is selected from the group consisting of Ser, Thr, Met, Trp, and Tyr.

9. A mutant staphylococcal alpha hemolysin polypeptide comprising a heterologous amino acid, wherein the heterologous amino acid binds an analyte and wherein the polypeptide assembles into a heteroheptameric pore assembly in the presence of a plurality of wild type staphylococcal alpha hemolysin polypeptides and wherein the amino acid is selected from the group consisting of Glu, Asp, Cys, His.

10. The polypeptide of claim 9, wherein said amino acid is His.

11. A staphylococcal alpha hemolysin (αHL) polypeptide comprising at least two non-consecutive heterologous amino acids in a stem domain of said polypeptide, wherein each of said heterologous amino acids binds an organic molecule.

12. The polypeptide of claim 11, wherein said organic molecule is an explosive.

13. The polypeptide of claim 12, wherein said polypeptide is 123W/125W.

14. The polypeptide of claim 11, wherein said amino acids occupy two or more of the following positions of SEQ ID NO: 1: 111, 113, 111, 117, 119, 121, 123, 125, 127, 129, 131, 133, 131, 137, 139, 141, 143, 145, 147 or 149.

15. The polypeptide of claim 11, wherein said polypeptide further comprises a third heterologous amino acid at a site distant from said stem domain.

16. The polypeptide of claim 15, wherein said third heterologous amino acid is a Cys residue at position 292 of SEQ ID NO: 1.

17. A heptomeric pore assembly comprising a mutated staphylococcal αHL polypeptide (MUT), wherein the MUT is 123W/125W.

18. A digital biosensor device comprising a heptomeric pore assembly comprising a mutated staphylococcal αHL polypeptide (MUT), wherein the MUT is an analyte-binding αHL polypeptide comprising at least two nonconsecutive heterologous amino acids in the stem domain of the polypeptide, wherein each of the heterologous amino acids binds a metal.

19. The device of claim 18, wherein said device detects binding of a metal ion to said analyte-binding αHL polypeptide.

20. The device of claim 19, wherein said device detects a single channel current.

21. The device of claim 19, wherein said device detects a current through two or more channels.

22. A digital biosensor device comprising a heptomeric pore assembly comprising a mutated staphylococcal αHL polypeptide (MUT), wherein the MUT is an analyte-binding αHL polypeptide comprising a chelating molecule in the stem domain of the polypeptide.

23. The device of claim 22, wherein said device detects binding of a metal ion to said analyte-binding αHL polypeptide.

24. The device of claim 23, wherein said device detects a single channel current.

25. The device of claim 23, wherein said device detects a current through two or more channels.

* * * * *

UNITED STATES PATENT AND TRADEMARK OFFICE
CERTIFICATE OF CORRECTION

| | | |
|---|---|---|
| PATENT NO. | : 6,824,659 B2 | Page 1 of 1 |
| APPLICATION NO. | : 09/784985 | |
| DATED | : November 30, 2004 | |
| INVENTOR(S) | : Hagan Bayley et al. | |

It is certified that error appears in the above-identified patent and that said Letters Patent is hereby corrected as shown below:

On the title page item (73), insert:

--University of Massachusetts, Boston, MA (US); The Trustees of Columbia University in the City of New York, New York, NY (US); The Government of the United States of America, as represented by the Secretary of Commerce, Washington, DC (US)--

Signed and Sealed this

Twenty-seventh Day of November, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 293
<212> TYPE: PRT
<213> ORGANISM: Staphylococcus aureus

<400> SEQUENCE: 1

Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn
             20                  25                  30

Gly Met His Lys Lys Val Phe Tyr Ser Phe Ile Asp Asp Lys Asn His
         35                  40                  45

Asn Lys Lys Leu Leu Val Ile Arg Thr Lys Gly Thr Ile Ala Gly Gln
     50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 2
<211> LENGTH: 40
<212> TYPE: PRT
<213> ORGANISM: Staphylococcus aureus

<400> SEQUENCE: 2

Glu Tyr Met Ser Thr Leu Thr Tyr Gly Phe Asn Gly Asn Val Thr Gly
1               5                   10                  15

Asp Asp Thr Gly Lys Ile Gly Gly Leu Ile Gly Ala Asn Val Ser Ile
                20                  25                  30

Gly His Thr Leu Lys Tyr Val Gln
            35                  40
```